(12) United States Patent
Muse et al.

(10) Patent No.: US 11,354,319 B2
(45) Date of Patent: Jun. 7, 2022

(54) SYSTEMS AND METHODS FOR PROVIDING USER DATA TO FACILITY COMPUTING ENTITIES

(71) Applicant: Optum, Inc., Minnetonka, MN (US)

(72) Inventors: Jon Kevin Muse, Thompson Station, TN (US); Gregory J. Boss, Saginaw, MI (US); Vijay S. Nori, Roswell, GA (US); Martijn P. Van Overbeek, Chapel Hill, NC (US)

(73) Assignee: Optum, Inc., Minnetonka, MN (US)

( * ) Notice: Subject to any disclaimer, the term of this patent is extended or adjusted under 35 U.S.C. 154(b) by 172 days.

(21) Appl. No.: 16/777,784

(22) Filed: Jan. 30, 2020

(65) Prior Publication Data
US 2021/0240720 A1    Aug. 5, 2021

(51) Int. Cl.
*G06F 16/00* (2019.01)
*G06F 16/2457* (2019.01)
*G06F 16/2455* (2019.01)
*G06F 16/29* (2019.01)
*G06F 16/28* (2019.01)

(52) U.S. Cl.
CPC .. *G06F 16/24573* (2019.01); *G06F 16/24564* (2019.01); *G06F 16/288* (2019.01); *G06F 16/29* (2019.01)

(58) Field of Classification Search
CPC .......... G06F 16/24573; G06F 16/288; G06F 16/24564; G06F 16/29
USPC ...................................................... 707/769
See application file for complete search history.

(56) References Cited

U.S. PATENT DOCUMENTS

| 8,126,740 B2 | 2/2012 | Busch |
| 10,412,210 B2 | 9/2019 | Bjontegard |
| 2008/0270180 A1 | 10/2008 | Sholtis et al. |
| 2017/0147788 A1 | 5/2017 | Ohnemus et al. |

(Continued)

FOREIGN PATENT DOCUMENTS

IN    2015DE02991 A    3/2017

OTHER PUBLICATIONS

Shiklo, Boris, RFID and IoT in a smart hospital: benefits and challenges of smart patient tracking, Oct. 31, 2018, ScienceSoft, 9 pages, https://www.scnsoft.com/blog/rfid-and-iot-in-a-smart-hospital-benefits-and-challenges-of-smart-patient-tracking, Apr. 10, 2020.

*Primary Examiner* — Vincent F Boccio
(74) *Attorney, Agent, or Firm* — Alston & Bird LLP

(57) ABSTRACT

Various methods and systems for selectively and securely sharing user data to a facility in order to accommodate the specific needs of the user. The methods further correspond to receiving, from a computing entity, geographic location information corresponding to the geographic location of the computing entity which is associated with the user and transmitting a notification to the computing entity of a facility in proximity to the geographic location of the computing entity. The methods further include receiving, from the facility, a request for user data associated with the user of the computing entity that is applicable to the facility, generating a proposed user dataset in response to the request that satisfies the facility-specific user data parameters and transmitting the proposed user dataset that meets the facility-specific user data parameters for sharing with the facility when a relevance score exceeds a relevance threshold value and the sharing eligibility is approved.

17 Claims, 8 Drawing Sheets

(56) References Cited

U.S. PATENT DOCUMENTS

| | | |
|---|---|---|
| 2018/0018704 A1 | 1/2018 | Tunnell et al. |
| 2018/0039737 A1 | 2/2018 | Dempers et al. |
| 2018/0101652 A1 | 4/2018 | Kochura et al. |
| 2018/0196922 A1 | 7/2018 | Abuelsaad et al. |
| 2019/0073448 A1 | 3/2019 | Kochura et al. |
| 2019/0088373 A1 | 3/2019 | Sarmentero |
| 2019/0272602 A1 | 9/2019 | Ray et al. |
| 2020/0036709 A1* | 1/2020 | Mars .................. H04L 63/0861 |
| 2020/0275266 A1* | 8/2020 | Jakobsson ............... H04W 4/38 |

* cited by examiner

SYSTEMS AND METHODS FOR PROVIDING USER DATA TO FACILITY COMPUTING ENTITIES

BACKGROUND

When a user enters a facility, the facility (e.g., a business associated with a facility, employees associated with a facility, residents associated with a facility, and/or the like) has no knowledge of that user's possible medical needs (if any) whether those needs relate to allergies, elevated heart rate, disabilities, or other medical issues. Businesses would often want to accommodate visitors if certain limited and appropriate medical information were known. Such accommodations can be seen as thoughtful to some visitors, thereby improving the visitor's customer service experience, and encouraging repeat visits and/or recommendations to others.

Various user applications exist for autonomous user monitoring, diagnosis, and alerting. However, they do not facilitate smart data transfer communications between businesses and users in a given scenario, such as when a user with peanut allergies enters a Thai restaurant. There is, therefore, a need for systems and methods that capture appropriate user data for secure transmission to a business so as to accommodate a user's medical needs and preferences.

Applicant has identified a number of deficiencies and problems associated with conventional user monitoring, diagnosis, and alerting systems. Through applied effort, ingenuity, and innovation, many of these identified problems have been solved by developing solutions that are included in embodiments of the present invention, many examples of which are described in detail herein.

BRIEF SUMMARY

In general, embodiments of the present invention provide methods, apparatus, systems, computing entities, computing entities, and/or the like for selective and securely sharing user data to accommodate the specific needs of the user. In accordance with one aspect, a method is provided. In one embodiment, the method comprises receiving location information corresponding to the location of a user computing entity associated with a user; upon detecting the location information indicating the location of the user computing entity associated with the user is within a proximity distance of a facility, generating, in association with a facility computing entity associated with the facility, a request for user data associated with the user of the user computing entity that is applicable to the facility, wherein the request comprises facility-specific user data parameters corresponding to characteristics of the user as reflected by at least a portion of the user data; generating a proposed user dataset in response to the request that satisfies the facility-specific user data parameters; determining, based at least in part on the proposed user dataset that satisfies the facility-specific user data parameters and additional user data indicative of a current context of the user, a relevance score of the proposed user dataset that satisfies the facility-specific user data parameters; determining, sharing eligibility of the proposed user dataset that meets the facility-specific user data parameters based at least in part on user-specified eligibility criteria; and upon determining that the relevance score satisfies applicable relevance criteria, transmitting the proposed user dataset that meets the facility-specific user data parameters and satisfies the user-specified eligibility criteria.

In accordance with another aspect, a computer program product is provided. The computer program product may comprise at least one computer-readable storage medium having computer-readable program code portions stored therein, the computer-readable program code portions comprising executable portions configured to receive location information corresponding to the location of a user computing entity associated with a user; upon detecting the location information indicating the location of the user computing entity associated with the user is within a proximity distance of a facility, generate, in association with a facility computing entity associated with the facility, a request for user data associated with the user of the user computing entity that is applicable to the facility, wherein the request comprises facility-specific user data parameters corresponding to characteristics of the user as reflected by at least a portion of the user data; generate a proposed user dataset in response to the request that satisfies the facility-specific user data parameters; determine, based at least in part on the proposed user dataset that satisfies the facility-specific user data parameters and additional user data indicative of a current context of the user, a relevance score of the proposed user dataset that satisfies the facility-specific user data parameters; determine, sharing eligibility of the proposed user dataset that meets the facility-specific user data parameters based at least in part on user-specified eligibility criteria; and upon determining that the relevance score satisfies applicable relevance criteria, transmit the proposed user dataset that meets the facility-specific user data parameters and satisfies the user-specified eligibility criteria.

In accordance with yet another aspect, an apparatus comprising at least one processor and at least one memory including computer program code is provided. In one embodiment, the at least one memory and the computer program code may be configured to, with the processor, cause the apparatus to receive location information corresponding to the location of a user computing entity associated with a user; upon detecting the location information indicating the location of the user computing entity associated with the user is within a proximity distance of a facility, generate, in association with a facility computing entity associated with the facility, a request for user data associated with the user of the user computing entity that is applicable to the facility, wherein the request comprises facility-specific user data parameters corresponding to characteristics of the user as reflected by at least a portion of the user data; generate a proposed user dataset in response to the request that satisfies the facility-specific user data parameters; determine, based at least in part on the proposed user dataset that satisfies the facility-specific user data parameters and additional user data indicative of a current context of the user, a relevance score of the proposed user dataset that satisfies the facility-specific user data parameters; determine, sharing eligibility of the proposed user dataset that meets the facility-specific user data parameters based at least in part on user-specified eligibility criteria; and upon determining that the relevance score satisfies applicable relevance criteria, transmit the proposed user dataset that meets the facility-specific user data parameters and satisfies the user-specified eligibility criteria.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION

Figure 1:
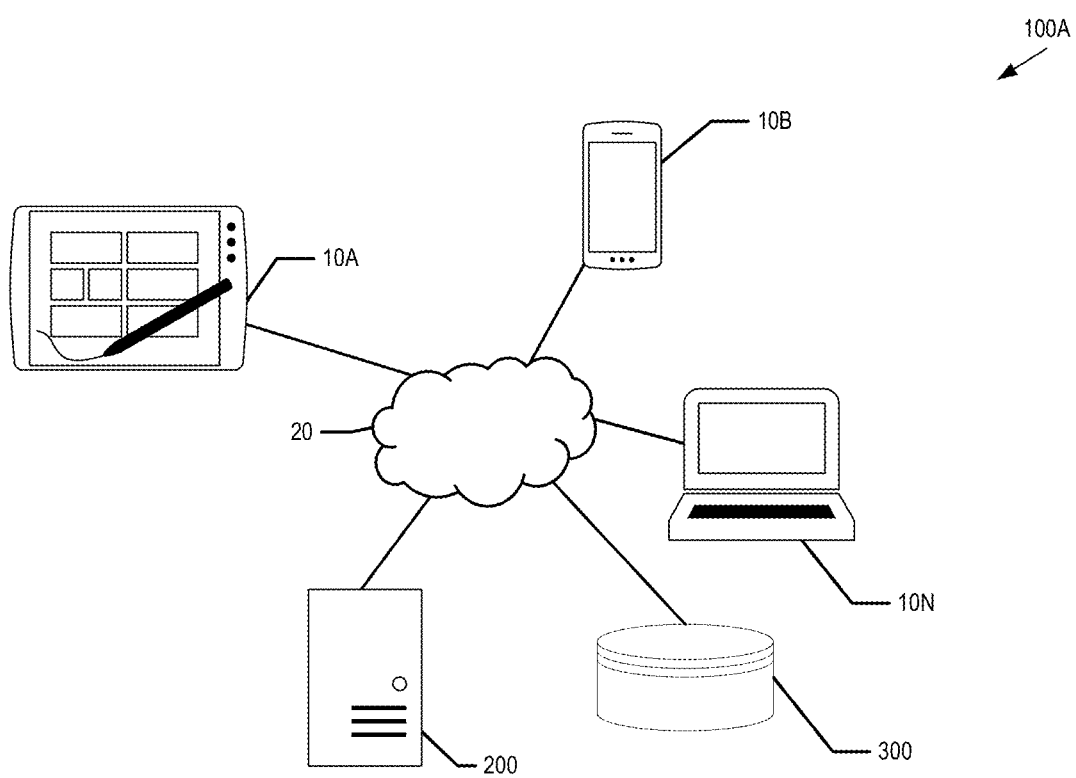
FIG. 1 is an exemplary overview of a system that can be used to practice embodiments of the present invention.

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout.

I. Overview

Discussed herein are configurations for capturing user's data (EMR data & real time wearable and/or IoT data indicative of real-time health characteristics of the user), a user's context (recent actions, activities, etc.), and current surroundings (e.g., ambient temperature, surrounding crowd size, and/or the like) via an Intelligent User Health Data Transfer (IDTS) system, which may be implemented within a closed-loop system (or otherwise within an existing communication configuration between a user's user computing entity and one or more facility computing entities) encompassing the user's user computing entity and the facility's user computing entity, such that the user's data is stored locally on the user's user computing entity (e.g., within and/or accessible via a corresponding app executing on the user computing entity for sharing user data in accordance with embodiments as discussed herein) and the user data is provided directly to the facility's user computing entity (e.g., for viewing and/or temporary access via an app executing at the facility's user computing entity. In other embodiments, the IDTS system may be implemented with a third-party implementation system configured to receive data from user's user computing entities and for reporting data deemed relevant to the facility's user computing entity. The IDTS system (whether implemented via a closed-system configuration or with an intermediary third-party system, collects user data in accordance with user preferences (e.g., the user specifies types of data to be collected, whether from sensors onboard the user computing entity, from sensors in communication with the user computing entity (e.g., wearable devices in communication with the user computing entity, from an operating system and/or other apps executing on the user computing entity, and/or the like), and enables such data to be transmitted to a facility's user computing entity upon determining such data is deemed relevant.

The system additionally detects the user's location (based on the user computing entity location) relative to one or more facilities to determine when user data may be provided to the facility's user computing entity. Upon detecting that the user is in proximity to a particular facility, the IDTS system analyzes the user data and determines what user data, such as what medical health information and/or risk variables to provide to a facility (e.g., a business, a residence, a warehouse, a recreational area, and/or the like) during the time period the person is in proximity of the facility's receiver. Such analysis may proceed based on one or more data transfers between the facility's and user's computing entities, and/or based on preferences stored at the intermediate third party system. Such preferences (and/or data communications) may be indicative of user data requested by the facility (e.g., via the facility's user computing entity). The IDTS system facilitates smart data transfer communications between facilities and users (or patients, the terms being used synonymously herein). The IDTS system captures user targeting parameters indicative of desired user data (e.g., sensitivities, intolerances, allergies, preexisting medical conditions, mobility limitations, etc.) set by the facilities. For example, a restaurant business might have targeting parameters dictating that food allergies be captured from the user, thereby enabling the restaurant to provide an allergy-free menu specifically tailored to the user. As such, the facility may not need obtain all user data that is collected on behalf of the user (e.g., by the user's user computing entity and/or at the third party intermediary system), but only certain data deemed important or relevant to the facility. The IDTS system (e.g., executing at the user's user computing entity or via the third party intermediary system) further selectively determines what user data, such as medical and user profile information to send to a facility's user computing entity based at least in part on the user's preference (while maintaining the user's anonymity in some cases). At least a portion of the determination of relevant information to provide to the facility's user computing entity may proceed in accordance with a machine-learning based relevance model configured to assign a relevance score to particular items of user data and to determine whether each item of user data is sufficiently relevant to be passed to the facility's user computing entity. The facility's user computing entity receives the selected user information, and the system (e.g., the third-party intermediary and/or the facility's user computing entity) determines what actions the facility should take to accommodate, protect, or benefit that user (e.g., alert staff of peanut allergy, seat user in a quiet location, provide separate wheel-chair accessible entrance, automatically change temperature of room, etc.) and provides a notification (e.g., via a user interface) indicative of recommended actions to be taken by the facility to accommodate the user. The IDTS system, in real time, analyzes the user's condition and context to determine current risk factors.

A. Technical Problem

When a user enters a facility (e.g., a business), the facility has no knowledge of that user's possible medical needs, such as allergies, elevated heart rate, disabilities, or other medical issues. Businesses would often want to accommodate users if certain limited and appropriate medical information were known. Similarly, users have well-established preferences in certain circumstances that facilities may desire to accommodate to build high levels of customer satisfaction.

However, because user visits to various facilities are generally unpredictable from the perspective of the facility (e.g., when a user will enter, how long the user will stay, what portions of the facility the user will visit, and/or the like), it is generally difficult to obtain meaningful information regarding a particular user prior to the user's visits. Moreover, facilities generally have limited options for obtaining information regarding users even while those users are physically located within the facility.

Moreover, because users have differing preferences on what personal data is shared and how that personal data is shared, secure measures must be provided when sharing data with facilities. Moreover, only user data relevant to a particular facility should be shared, so as to preserve a user's privacy regarding data deemed irrelevant to a facility.

B. Technical Solution

Accordingly, various embodiments utilize one or more of the following architectural advantages and security measures: a privacy model and sharing options, system configuration (e.g., a closed-loop system) for preventing unauthorized user data access, a third-party intermediary system for managing authorization to user data access, one or more industry protocol adoption to facilitate data transfers, user control of data access authorizations, and anonymity. In certain embodiments, user data, such as a user's medical data is not exchanged unknowingly or haphazardly with facilities (e.g., facility user computing entities) that the user visits. To this end, various security measures can be applied individually or layered to achieve higher levels of privacy.

In certain embodiments, a system is provided which limits all data exchange to only the user's user computing entity and the facility's user computing entity and may be implemented at least partially via an app created and/or managed by the facility (or created and/or managed by a third-party) and would require that the user to install the app and opt in to the terms and conditions set forth. In such embodiments, various executable models, electronic connections between computing entities, data transfers, and/or the like are executed and/or managed in accordance with apps stored and operated locally on user computing entities at the user's device and the facility's device, respectively. For example, the user may provide preferences regarding the collection and/or sharing of particular user data, such as medical data, within in the locally executing app. When the app determines the user to be at or close to said facility (e.g., by accessing one or more operating system-specific attributes of the user computing entity), the user computing entity of the user may receive that facility's requested attributes and the locally executing app may be configured to determine relevancy and eligibility of user data transfer, and then exchange the user data deemed sufficiently relevant and eligible for data transfer. In some embodiments, the app may allow a user computing device to communicate with the facility's device and to allow data sharing as long as both users have the app. For example, a user computing device may automatically connect to a facility's WiFi network based on their previous association using the user computing device's access credentials. For example, after the user computing device is identified and establishes an automatic connection to the facility's WiFi, the system may determine the facility is associated with a known company. If the company is known, the system may provide communication means via the app between the user computing device and the facility's device.

The IDTS system may further coordinate with a trusted medical provider or insurer (or other trusted third-party embodied as a computing entity) to act as an intermediary system for data exchange, such that the intermediary system may execute any included models, and the intermediary may maintain appropriate data exchange connections with included user computing entities participating in the data exchange configurations discussed herein. All data in the setup and operational methods discussed below may be sent and received via the trusted third-party. The third-party may perform the tasks of authenticating users and facilities and may optionally aggregate multiple facility locations into a single authentication/authorization model (e.g. for nationwide chain stores). The third-party intermediary system may also provide a container which enables access to the data after suitable authentication and shuts off the access after a specified trigger event, for example, after the end of a game at a sports venue. The third-party intermediary system may execute analytics in the container and will only be able to retrieve summary information on which they can act.

In embodiments, the IDTS system may augment existing protocols like 802.11 (e.g. Wi-Fi) with a standard that allows for secured user data, such as user medical data exchange. In this approach, the facility's broadcast for specific user data (e.g., medical data) adheres to an industry standard in order to be received by compliant Wi-Fi endpoints. This exchange could employ standard encryption, authentication, and/or encapsulation methods to ensure that data is only being sent to those facilities that the user pre-authorizes. In this approach, the medical data exchange enjoys the already broadly accepted security implements of Wi-Fi which allows users to opt-in to connecting to various facilities' Wi-Fi. For example, a user enters a coffee shop with free Wi-Fi. Only if the user has already opted in to join the coffee shop's Wi-Fi network will the subsequent medical data exchange techniques take place.

Moreover, users of the IDTS system can specify in advance exactly which facility, type of facility and associated medical attributes are permitted for transmission. The system also causes generation of a visual (or audible) notification on the user's device (e.g., smart phone), thereby providing a user interface for the user to manually opt-in to sending medical data. In this case, each notification displays what information the system has calculated should be sent with an option for the user to modify the list of information to be transmitted manually and/or select "OK" to send.

In certain embodiments, the IDTS system may evaluate the facility environment and determine if the medical data can be safely sent in an anonymous mode. For example, the IDTS system may implement a time delay to mask the identity of a person presently entering a facility or it can detect the number of users present in the building (optionally with specific attributes similar to the user) and if there is a sufficient number of people it can send the data without identifiable attributes.

II. Computer Program Products, Methods, and Computing Entities

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing entities, computing entities, and/or the like. As such, embodiments of the present invention may take the form of an apparatus, system, computing entity, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing entities, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

III. Exemplary System Architecture

FIG. 1 provides an illustration of an exemplary embodiment of the present invention. FIG. 1 shows system 100 including an example network architecture for a system, which may include one or more devices and sub-systems that are configured to implement some embodiments discussed herein. As shown in FIG. 1, the system 100 may comprise one or more servers 30, one or more user computing entities 10A-10N, one or more networks 20, and/or the like. Each of the components of the system may be in electronic communication with, for example, one another over the same or different wireless or wired networks 20 as discussed herein.

In the example illustrated embodiment of FIG. 1, the system 100 may include IDTS system 400, which can be embodied as a part of, for example, circuitry 200 and/or database, among other things (not shown). The IDTS system 400 may include any suitable network server and/or other type of processing device. In some embodiments, the IDTS system 400 may determine and transmit commands and instructions for training data models, generating optimal health and risk strategies to safeguard a user using data stored via a data monitoring database 300 (shown in FIG. 3) which may be stored as a part of and/or in communication with one or more user computing entities 10A-10N and/or the IDTS system 400. The data monitoring database 300 includes information accessed and stored by the user computing entity 10 to facilitate the operations of the IDTS system 400.

IDTS system 400 can communicate with one or more user computing entities 10A-10N and/or other computing entities via communications network 20, and a plurality of user computing entities 10A-10N may communicate with one another and/or other computing entities via the network 20. In this regard, communications network 20 may include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, etc.). For example, communications network 20 may include a cellular telephone, an 802.11, 802.16, 802.20, and/or WiMax network. Further, the communications network 20 may include a public network, such as the Internet, a private network, such as an intranet, or combinations thereof, and may utilize a variety of networking protocols now available or later developed including, but not limited to TCP/IP based networking protocols. For instance, the networking protocol may be customized to suit the needs of the group-based communication interface. In some embodiments, the protocol is a custom protocol of JSON objects sent via a Websocket channel. In some embodiments, the protocol is JSON over RPC, JSON over REST/HTTP, and the like.

User computing entities 10A-10N and/or IDTS system 400 may each be implemented as one or more computers, computing entities, desktop computers, mobile phones, tablets, phablets, notebooks, laptops, distributed systems, gaming consoles (e.g., Xbox, Play Station, Wii), watches, glasses, iBeacons, proximity beacons, key fobs, radio frequency identification (RFID) tags, ear pieces, scanners, televisions, dongles, cameras, wristbands, wearable items/devices, items/devices, vehicles, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. The depiction in FIG. 1 of "N" user computing entities is merely for illustration purposes. Any number of users and/or user computing entities 10 may be included in the system for accessing and/or implementing aspects of the IDTS system 400 discussed herein (e.g., via one or more interfaces). In one embodiment, the user computing entities 10A-10N may be configured to display or provide IDTS system interface on a display of the user computing entity for viewing, creating, editing, and/or otherwise interacting with one or more notifications, which may be provided or pushed by the IDTS system 400 (and may be stored locally at one or more user computing entities 10A-10N). According to some embodiments, the IDTS system 400 may be configured to cause display or presentation of an interface for viewing, creating, editing, and/or otherwise interacting with one or more data transfer notifications, health action plans, and/or risk assessments.

As indicated above, the user computing entities 10A-10N may be any computing entity as defined above. Electronic data received by the IDTS system 400 from the user computing entities 10A-10N may be provided in various forms and via various methods. For example, the user computing entities 10A-10N may include desktop computers, laptop computers, smartphones, netbooks, tablet computers, wearables, and the like. In embodiments where a user computing entity 10A-10N is a mobile device, such as a smart phone or tablet, the user computing entity 10A-10N may execute an "app" such as the IDTS application to interact with the IDTS system 400. Such apps are typically designed to execute on mobile devices, such as tablets or smartphones. For example, an app may be provided that executes on mobile device operating systems such as iOS®, Android®, or Windows®. These platforms typically provide frameworks that allow apps to communicate with one another and with particular hardware and software components of mobile devices. For example, the mobile operating systems named above each provide frameworks for interacting with location services circuitry, wired and wireless network interfaces, user contacts, and other applications. Communication with hardware and software modules executing outside of the app is typically provided via application programming interfaces (APIs) provided by the mobile device operating system.

Additionally or alternatively, the user computing entity 10A-10N may interact with the IDTS system 400 via a web browser. As yet another example, the user computing entity 10A-10N may include various hardware or firmware designed to interface with the IDTS system 400. As also shown in FIG. 1, a plurality of sensors 15A-15N (which in certain embodiments may be a part of one or more user computing entities 10A-10N) provide information to the IDTS system 400 (e.g., via network 20). For example, the sensors 15A-15N may comprise motion sensors, power sensors for various devices (e.g., a television, a stereo, a video game console, one or more lights, one or more fans, a stove, a treadmill, an exercise bicycle, and/or the like), temperature sensors, and/or the like, proximity sensors (e.g., Bluetooth sensors, near field communication (NFC) sensors), voice-activated sensors (e.g., voice activated personal digital assistants), electric-car charging sensors, and/or the like. It should be understood that these sensors, as well as other sensors discussed herein, are provided merely as examples, and any sensors that may be indicative of the location and/or activity of a user may be provided. In some embodiments, the IDTS system 400 may be configured to be in communication with the one or more user computing entities 10A-10N to establish a cloud-based, device-based, and/or or fog-based (e.g., a networked system within a home, building, facility, and/or the like, edge device, fog device or full public cloud) system for a user. The plurality of sensors 15A-15N may be embodied by Internet of Things (IoT) devices.

A. Exemplary Circuitry of an IDTS System

Figure 2A:
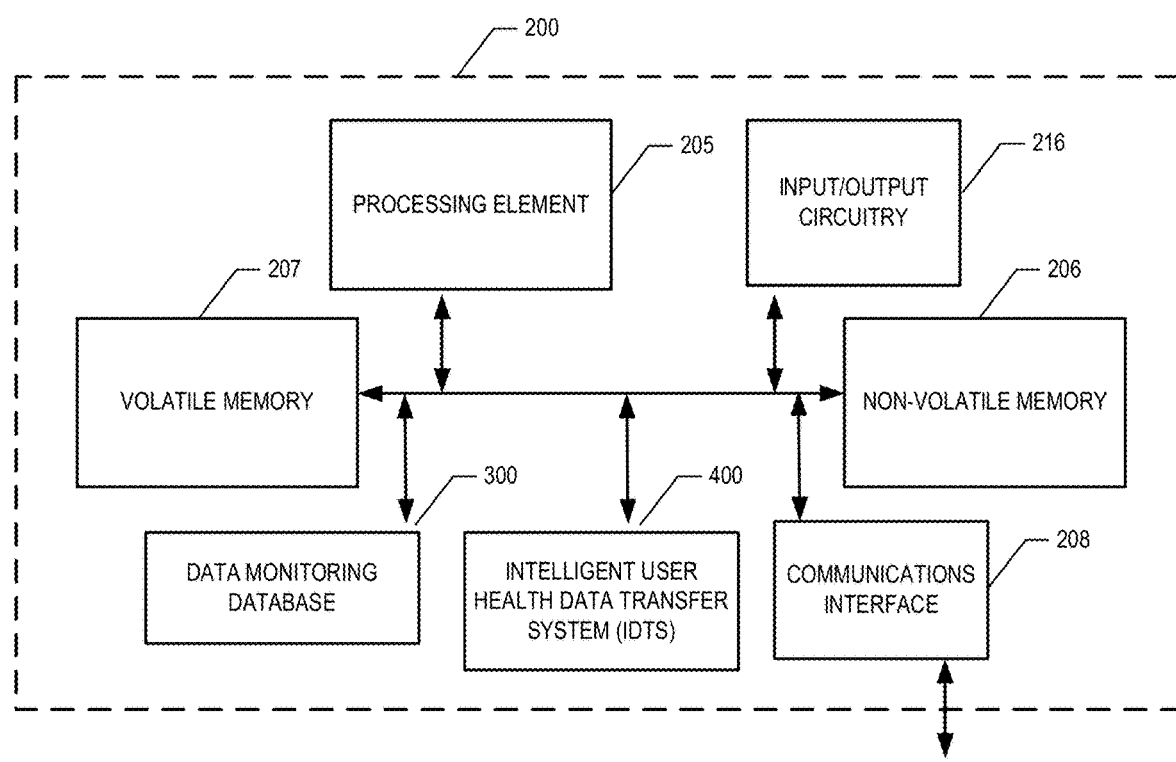
FIG. 2A illustrates an example user computing entity in accordance with some embodiments discussed herein.

FIG. 2A provides a schematic of circuitry 200, some or all of which may be included in, for example, IDTS system 400 and/or user computing entities 10A-10N. Any of the aforementioned systems or devices may include the circuitry 200 and may be configured to, either independently or jointly with other devices in a network 20 perform the functions of the circuitry 200 described herein. In general, the terms computing entity, entity, device, system, and/or similar words used herein interchangeably may refer to, for example, one or more computers, computing entities, desktop computers, mobile phones, tablets, phablets, notebooks, laptops, distributed systems, items/devices, terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As illustrated in FIG. 2A, in accordance with some example embodiments, circuitry 200 can includes various means, such as processing element 205, volatile memory 207, non-volatile memory 206, communications interface 208, data monitoring database 300, intelligent user health data transfer system (IDTS) 400, and/or input/output circuitry 216. As referred to herein, "circuitry" includes hardware, software and/or firmware configured to perform one or more particular functions. In this regard, the means of circuitry 200 as described herein may be embodied as, for example, circuitry, hardware elements (e.g., a suitably programmed processor, combinational logic circuit, and/or the like), a computer program product comprising computer-readable program instructions stored on a non-transitory computer-readable medium (e.g., non-volatile memory 206) that is executable by a suitably configured processing device (e.g., processing element 205), or some combination thereof.

Input/output circuitry 216 may be in communication with processing element 205 to receive an indication of a user input and/or to provide an audible, visual, mechanical, or other output to a user (e.g., provider and/or consumer). As such, input/output circuitry 216 may include support, for example, for a keyboard, a mouse, a joystick, a display, a touch screen display, a microphone, a speaker, a RFID reader, barcode reader, biometric scanner, and/or other input/output mechanisms. In embodiments wherein circuitry 200 is embodied as a server or database, aspects of input/output circuitry 216 may be reduced as compared to embodiments where circuitry 200 is implemented as an end-user machine (e.g., consumer device and/or provider device) or other type of device designed for complex user interactions. In some embodiments (like other components discussed herein), input/output circuitry 216 may even be eliminated from circuitry 200. Alternatively, such as in embodiments wherein circuitry 200 is embodied as a server or database, at least some aspects of input/output circuitry 216 may be embodied on an apparatus used by a user that is in communication with circuitry 200. Input/output circuitry 216 may be in communication with the volatile memory 207, non-volatile memory 206, communications interface 208, and/or any other component(s), such as via a bus. One or more than one input/output circuitry and/or other component can be included in circuitry 200.

Data monitoring database 300 and IDTS system 400 may also or instead be included and configured to perform the functionality discussed herein. In some embodiments, some or all of the functionality may be performed by processing element 205. In this regard, the example processes and algorithms discussed herein can be performed by at least one processing element 205, data monitoring database 300, and/or IDTS system 400. For example, non-transitory computer readable media can be configured to store firmware, one or more application programs, and/or other software, which include instructions and other computer-readable program code portions that can be executed to control each processor (e.g., processing element 205, data monitoring database 300, and/IDTS system 400) of the components of circuitry 200 to implement various operations, including the examples shown above. As such, a series of computer-readable program code portions are embodied in one or more computer program goods and can be used, with a computing entity, server, and/or other programmable apparatus, to produce machine-implemented processes.

As indicated, in one embodiment, circuitry 200 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the circuitry 200 may communicate with other computing entities, one or more user computing entities 10A-10N, and/or the like.

As shown in FIG. 2A, in one embodiment, the circuitry 200 may include or be in communication with one or more processing elements 205 (also referred to as processors, processing circuitry, and/or similar terms used herein interchangeably) that communicate with other elements within the circuitry 200 via a bus, for example, or network connection. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the circuitry 200 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 206 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably and in a general sense to refer to a structured or unstructured collection of information/data that is stored in a computer-readable storage medium.

Non-volatile memory 206 may also be embodied as a data storage device or devices, as a separate database server or servers, or as a combination of data storage devices and separate database servers. Further, in some embodiments, non-volatile memory 206 may be embodied as a distributed repository such that some of the stored information/data is stored centrally in a location within the system and other information/data is stored in one or more remote locations. Alternatively, in some embodiments, the distributed repository may be distributed over a plurality of remote storage locations only. An example of the embodiments contemplated herein would include a cloud data storage system maintained by a third party provider and where some or all of the information/data required for the operation of the relevancy prediction system may be stored. As a person of ordinary skill in the art would recognize, the information/data required for the operation of the relevancy prediction system may also be partially stored in the cloud data storage system and partially stored in a locally maintained data storage system.

Non-volatile memory 206 may include information/data accessed and stored by the IDTS system 400 to facilitate the operations of the system. More specifically, non-volatile memory 206 may encompass one or more data stores configured to store information/data usable in certain embodiments.

B. Exemplary User Computing Entity

Figure 2B:
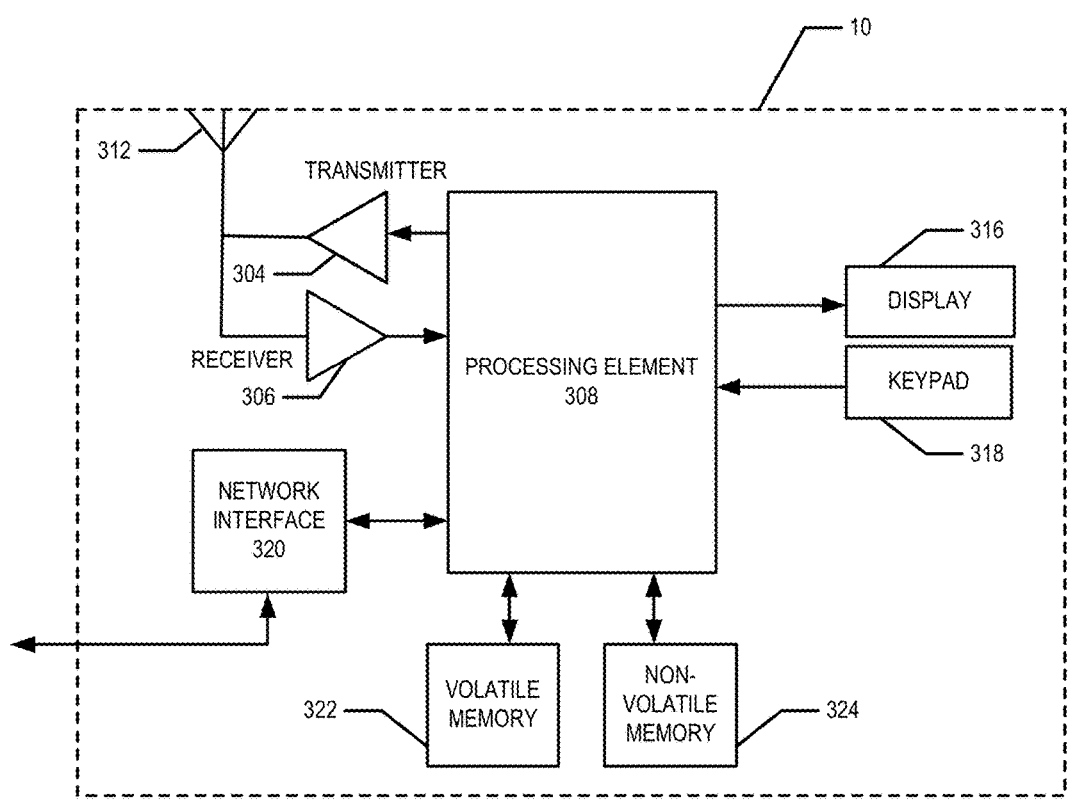
FIG. 2B illustrates an example user computing entity in accordance with some embodiments discussed herein.

FIG. 2B provides an illustrative schematic representative of user computing entity 10A-10N that can be used in conjunction with embodiments of the present invention. As shown in FIG. 2B, a user computing entity 10 can include an antenna 313, a transmitter 305 (e.g., radio), a receiver 307 (e.g., radio), and a processing element 309 that provides signals to and receives signals from the transmitter 305 and receiver 307, respectively. The signals provided to and received from the transmitter 305 and the receiver 307, respectively, may include signaling information/data in accordance with an air interface standard of applicable wireless systems to communicate with various entities, such as an IDTS system 400, another user computing entity 10, and/or the like. In this regard, the user computing entity 10 may be capable of operating with one or more air interface standards, communication protocols, modulation types, and access types. More particularly, the user computing entity 10 may operate in accordance with any of a number of wireless communication standards and protocols. In a particular embodiment, the user computing entity 10 may operate in accordance with multiple wireless communication standards and protocols, such as GPRS, UMTS, CDMA2000, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 10 can communicate with various other entities using concepts such as Unstructured Supplementary Service information/data (USSD), Short Message Service (SMS), Multimedia Messaging Service (MIMS), Dual-Tone Multi-Frequency Signaling (DTMF), and/or Subscriber Identity Module Dialer (SIM dialer). The user computing entity 10 can also download changes, add-ons, and updates, for instance, to its firmware, software (e.g., including executable instructions, applications, program modules), and operating system.

According to one embodiment, the user computing entity 10 may include location determining aspects, devices, modules, functionalities, and/or similar words used herein interchangeably. For example, the user computing entity 10 may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data may be determined by triangulating the computing entity's position in connection with a variety of other systems, including cellular towers, Wi-Fi access points, and/or the like. Similarly, the user computing entity 10 may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing entities (e.g., smartphones, laptops) and/or the like. For instance, such technologies may include iBeacons, Gimbal proximity beacons, BLE transmitters, NFC transmitters, and/or the like. These indoor positioning aspects can be used in a variety of settings to determine the location of someone or something to within inches or centimeters.

The user computing entity 10 may also comprise a user interface device comprising one or more user input/output interfaces (e.g., a display 316 and/or speaker/speaker driver coupled to a processing element 309 and a touch screen, keyboard, mouse, and/or microphone coupled to a processing element 309). For example, the user output interface may be configured to provide an application, browser, user interface, dashboard, webpage, and/or similar words used herein interchangeably executing on and/or accessible via the user computing entity 10 to cause display or audible presentation of information/data and for user interaction therewith via one or more user input interfaces. As just one specific example, the user computing entity 10 may be configured to output various interface screens associated with a IDTS application, which may provide various setup/registration screens and/or may provide one or more health risk alerts for a user of the user computing entity. The user input interface can comprise any of a number of devices allowing the user computing entity 10 to receive data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 10 and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the user computing entity 10 can collect information/data, user interaction/input, and/or the like.

The user computing entity 10 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the user computing entity 10. Again, as a specific example, the user computing entity memory storage areas (encompassing one or both of the volatile memory 322 and/or non-volatile memory 324) may store the IDTS application thereon, which itself may encompass a one or more artificial intelligence and/or machine-learning algorithms. The memory storage areas discussed herein may further encompass one or more aspects of a data monitoring database 300, as discussed in greater detail herein (however the sensing data monitoring database 300 may be stored in association with the IDTS system 400 in certain embodiments).

In one embodiment, the IDTS system 400 may further include or be in communication with volatile media (also referred to as volatile storage, memory, memory storage, memory circuitry and/or similar terms used herein interchangeably). In one embodiment, the volatile storage or memory may also include one or more volatile storage or memory media 207 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory media may be used to store at least portions of the databases, database instances, database management system entities, data, applications, programs, program modules, scripts, source code, object code, byte code, compiled code, interpreted code, machine code, executable instructions, and/or the like being executed by, for example, the processing element 208. Thus, the databases, database instances, database management system entities, data, applications, programs, program modules, scripts, source code, object code, byte code, compiled code, interpreted code, machine code, executable instructions, and/or the like may be used to control certain aspects of the operation of the IDTS system 400 with the assistance of the processing element 205 and operating system.

As indicated, in one embodiment, the IDTS system 400 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the IDTS system 400 may communicate with computing entities or communication interfaces of other computing entities, user computing entities 10, and/or the like.

As indicated, in one embodiment, the IDTS system 400 may also include one or more network and/or communications interfaces 208 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the IDTS system 400 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol. The IDTS system 400 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

C. Exemplary Data Monitoring Database

Figure 3:
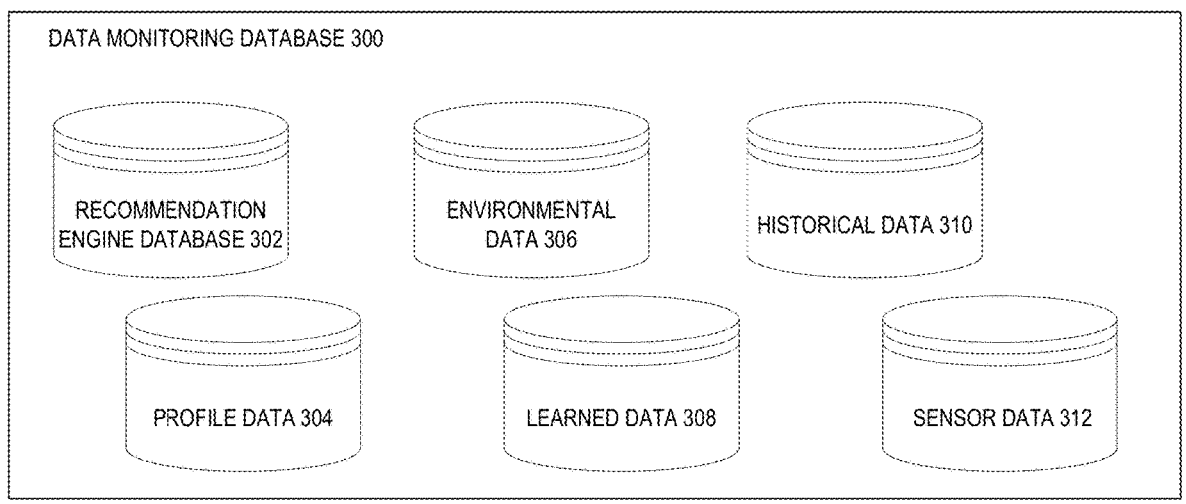
FIG. 3 illustrates an example data monitoring database in accordance with some embodiments discussed herein.

In some embodiments, a data monitoring database 300 may be provided that includes a recommendation engine database 302, profile data 304, environmental data 306, learned data 308, historical data 310, and/or sensor data 312 as depicted in FIG. 3. As discussed herein, the data monitoring database 300 may be provided within memory associated with one or more user computing entities 10A-10N and/or the IDTS system 400. As a specific example, portions of data stored within the data monitoring database 300 may be stored locally at one or more user computing entities 10A-10N corresponding to particular users and/or facilities, particularly in embodiments implemented as systems for data exchange only between a user's user computing entity and a facility's user computing entity and/or otherwise for data exchange via existing data communication channels between the user's user computing entity and the facility's user computing entity. In other embodiments, data stored within the data monitoring database 300 may be stored within a memory storage area accessible to a third-party intermediary system facilitating user data exchange between a user's user computing entity (and/or a user's profile) and a facility's user computing entity. In the latter embodiments, the third-party intermediary may be configured to provide desired encryption, privacy, and/or anonymity configurations applicable to a particular data exchange as discussed herein.

Profile data 304 corresponding to an individual user (referred to as user profile data), in some embodiments, may include user data such as medical data, data indicative of an ideal medicinal schedule, biographical data and/or preference data associated with individual users or groups of users. The user data included within profile data 304 may comprise stagnant data (e.g., data that does not change overtime except upon the occurrence of user-initiated interactions to modify the stagnant data), such as historical medical data, historical identification data, and/or the like. The user data included within the profile data 304 may additionally or alternatively comprise real-time data, such as data detected by one or more sensors in association with the user (e.g., real-time changes to the moving average heartrate of the user over a recent period of time). Moreover, the profile data 304 as discussed herein may comprise or more patient preferences, such as preferences regarding the sharing of user data with one or more facility user computing entities. In an example embodiment, the profile data 304 includes a set of rules for sharing user data. Rules for whether to share and/or how to share user data may vary based at least in part on data indicative of a facility type. For example, a patient may specify a rule that the IDTS system 400 can share all food allergy data with restaurant type facilities but not coffee shop type facilities. Another example rule can be set by the patient to always ask the patient if user data can be shared during an initial visit of the patient with a particular facility. Any number of rules may be set by the user and enforced by the IDTS system 400. As discussed herein, such profile data 304 may be supplemented with additional contextual data that may be obtained from any of a variety of data sources, such as ambient conditions (e.g., temperature, humidity, time-of-day, ambient lighting, and/or the like, which may be obtained from one or more sensors or external systems), nearby crowd size, and/or the like. Such additional contextual data may also be stored as environmental data, as discussed in further detail below.

The profile data may be associated with a unique user identifier (e.g., a username, an email address, a social security number, and/or the like) corresponding with a particular user.

In various embodiments, profile data 304 may be implemented as facility profile data corresponding to one or more facility profiles as discussed herein, and may comprise data indicative of various characteristics of a facility. Moreover, the facility profile data corresponding to a particular facility may additionally comprise data indicative of desired user data to be shared with the facility by and/or on behalf of a user's user computing entity. The desired user data may be reflective of data the facility may utilize to accommodate the user's visit to the facility. For example, the desired user data from a restaurant facility may comprise data indicative of a user's food allergies. In various embodiments, the desired user data as reflected within the facility profile data may be generated manually, for example, based at least in part on user input provided by a representative of the facility indicative of desired user data. In other embodiments (or after sufficient data is generated to support such a configuration), the desired user data may be generated based at least in part on the results of automated models (e.g., machine-learning based models) considering additional characteristics of the facility as reflected within the facility data.

Environmental data 306 may include anything that can be measured or captured in an environment and/or indicative of the context of the environment, such as a level of illumination, a level and spectrum of background noises, an activation state of a device within the environment (e.g., TV, audio streaming device, heating state from connected thermostat, motion from third party home automation systems, power sensing level from whole-home power sensors or individual plug socket power sensing devices), and/or a user's proximity to an object or device. The environmental data 306 may be associated with a particular profile of a facility in certain embodiments.

Learned data 308 may comprise one or more trained models (e.g., trained via one or more machine-learning configurations), such as for assigning relevance scores to particular user data to determine whether such data is sufficiently relevant to a particular facility to justify transmission to the facility. Such learned data 308 may be generated based at least in part on user preferences of one or more users, requested data of one or more facilities, contextual data, environmental data, and/or the like.

Sensor data 312 may include information received from various sensors available in the environment and/or associated with one or more user's user computing entities. Such sensors may be used for collecting status and/or usage data of monitored objects (e.g., meteorological data and water data, such as temperature, humidity; connected toothbrush usage; connected water bottle water consumption; connected coffee machine usage state; mattress pressure sensor sleep state reading; exercise regime participation as reported by a Cardio Vascular Rehabilitation system), interaction data (e.g., Virtual Personal Assistant (VPA) interactions; Medication dispenser interactions), and/or data from wearables (e.g., user computing entities such as phones, tablets, headsets, and the like to capture activity from accelerometers, screen state, particular app usage). Additionally or alternatively, the sensor data 312 provides any additional sensor information needed by the processing element 205 which provides additional information in collecting activity and context data.

Historical data 310 may include secure user electronic medical records comprising an electronic health record (EHR), also known as an electronic medical record (EMR), which is a collection of electronically stored information about an individual user's medical history. EHRs may contain a broad range of data, including demographics, medical history, medication history, allergies, immunization records, laboratory test results, radiology images, vital signs, personal statistics like age and weight, and billing information. Historical data 310 is retrieved via secure channels (e.g., HTTPS and TLS), and stored medical record data is in encrypted form. As discussed herein, the historical data 310 may be stored within profile data corresponding to a particular user, for example, within a local data storage environment of a user computing entity and/or within a memory storage area accessible to the third party intermediary system as discussed herein. In some embodiments, the IDTS system 400 may be configured to retrieve, access, or otherwise obtain user electronic medical records during a user registration process (e.g., in real-time, during batch user data retrieval processes, and/or the like). Under such configurations, the user data may be stored in association with the IDTS system 400 for later access (e.g., during an instance in which a user approaches a facility). Additionally, the IDTS system 400 may be configured to access data via a patient portal account so as to enable the patient to login and retrieve current and/or updated patient health records.

Further, the IDTS system 400 is configured to control access to the data monitoring database 300 such that only authorized users can cause creation of entries therein and to alter certain data of the data monitoring database 300. The IDTS system 400 is configured to be HIPAA compliant to maintain the privacy and security of individually identifiable medical record information. Accordingly, the IDTS system 400 may include customizable user settings to change privacy settings and actively control the amount of personal information that may be accessible to the IDTS system 400 or any other component of the IDTS system 400. It will be appreciated that digital precautions, including encryption, will be implemented for such personal information to protect against identity theft and multiple levels of permissions would be required to access such sensitive information.

The data monitoring database 300 may include a recommendation engine database 302 which provides information needed by the IDTS system 400 in recommending and/or predicting a strategy (e.g., using machine learning) to accommodate a user's medical needs and/or preferences.

In some embodiments, the data monitoring database 300 may further comprise provider information/data, member information/data, transaction information/data, communication information/data, and/or the like. Provider information/data comprises identifying information/data indicative of various providers, such as healthcare services providers associated with a particular user. The term provider is used generally to refer to any person or entity that provides goods, services, and/or the like. For example, the provider information/data may comprise provider identifiers, provider locations, provider relevancy scores, and/or the like. The provider information/data may further comprise provider flag information/data providing an indicator conveying that the provider is involved in an ongoing investigation or may need the provider's claims flagged for overpayment or fraud review.

The data monitoring database 300 may comprise member information/data, such as membership information relevant to a user and indicative of one or more healthcare programs, payment programs, and/or the like to which the user is a member. The member information/data may comprise information/data for a member, such as age, gender, poverty rates, known health conditions, home location, profession, access to medical care, medical history, claim history, member identifier (ID), and/or the like. A relevancy score may identify the predicted level of interest or relevance to the member.

Transaction information/data may comprise claim information/data indicative of claims filed on behalf of a provider for services or products. Examples of providers include medical doctors, nurse practitioners, physician assistants, nurses, other medical professionals practicing in one or more of a plurality of medical specialties (e.g., psychiatry, pain management, anesthesiology, general surgery, emergency medicine, etc.), hospitals, urgent care centers, diagnostic laboratories, surgery centers, and/or the like. Moreover, the claim information/data may further comprise prescription claim information/data. Prescription claim information/data may be used to extract information/data such as the identity of entities that prescribe certain drugs and the pharmacies who fulfill such prescriptions. The claim information/data may also comprise communication flag information/data indicative of whether there are one or more communication logs associated with the claim. Such claim information may be incorporated into a user's profile data, for example, so as to reflect specific medical conditions corresponding to the user.

The data monitoring database 300 may further store communication information/data used by the IDTS system 400. For example, the communication information/data stored by the data store may comprise the type of communication, the transaction (e.g., claim) to which it relates, the date of the communication, the time of the communication, the user (e.g., provider, member, insurance company) associated with the communication, and/or the like.

As will be appreciated, one or more of the analytic computing entity's components may be located remotely from other server components, such as in a distributed system. Furthermore, one or more of the components may be aggregated and additional components performing functions described herein may be included in the IDTS system 400. Thus, the IDTS system 400 can be adapted to accommodate a variety of needs and circumstances.

Moreover, although the foregoing describes the storage of data within a data monitoring database 300, it should be understood that certain data may be stored at other computing entities, such as at one or more user computing entities 10. For example, data corresponding to a particular user may be stored locally on a user computing entity 10 carried by the user computing entity 10. In such embodiments, data to be provided to a facility as discussed herein may be provided directly from the user computing entity 10 to the facility's computing entities.

D. Exemplary Functionality of an Intelligent User Health Data Transfer System (IDTS)

The IDTS system 400 can be configured to selectively and securely share user data with a facility (e.g., directly to a facility's user computing entity), so as to enable the facility to accommodate specific needs of the user (as determinable by the user data) while the user is located within the facility. In certain embodiments, the IDTS system 400 may be embodied as a server and/or any other computing entity having one or more components as discussed above in reference to user computing entities 10A-10N. In other embodiments, the IDTS system 400 may be embodied as user computing entities associated with an individual user and/or an individual facility, thereby enabling a system configuration in which data is shared only between the user's user computing entity and a relevant facility's user computing entity. Moreover, the IDTS system 400 may be in communication (e.g., via communications interface 208) with (and/or embodied as least partially as) one or more user computing entities 10A-10N (e.g., user computing entities operated by individual users and/or user computing entities operated by one or more facilities) to receive and/or transmit a proposed user dataset that meets the facility-specific user data parameters (e.g., indicative of desired user data) for sharing with the facility upon determining that sharing eligibility criteria are satisfied, for example, when a relevance score generated for a particular item of user data on behalf of a facility satisfies relevance criteria (e.g., the relevance score exceeds a relevance threshold value). The facility-specific user data parameters control search operations conducted by the IDTS system 400. For example, the facility may specify a variety of facility-specific user data parameters or keywords (e.g., allergy, disability, heart condition, etc.) indicative of particular user data requested, which correlates to a search request to be carried out by the IDTS system 400 to search within user data objects of the data monitoring database 300. In addition, the IDTS system 400 may associate the facility-specific user data parameters with a facility type, recall previously saved facility-specific user data parameters based on facility type, and/or modify the facility-specific user data parameters.

As a specific example of the implementation of system, the facility-specific user data parameters may be stored and/or maintained locally at facility user computing entities (e.g., embodying a portion of the functionality of the IDTS system 400). The facility user computing entity, upon detecting the presence of a user's user computing entity, may transmit data indicative of the user data parameters to the user's user computing entity (e.g., embodying another portion of the functionality of the IDTS system 400), which may implement a trained model for determining whether one or more items of user data stored locally at the user's user computing entity and satisfying various user data parameters has a relevance score satisfying relevance criteria for providing the item of user data to the facility user computing entity.

As a specific example of the implementation of a system incorporating a third-party intermediary system, the third-party intermediary system may identify the facility-specific user data parameters (e.g., stored within a profile at the third-party intermediary system). Upon the third-party intermediary system receiving data indicating that a particular user is proximate the facility (e.g., within data transmission range, within a geofenced around surrounding the facility, and/or the like), the third-party intermediary system retrieves user-specific data stored within a user data profile. The third party intermediary system may execute a trained model for determining whether one or more items of user data stored within the user's data profile and satisfying various user data parameters has a relevance score satisfying relevance criteria for providing the item of user data to the facility user computing entity.

In certain embodiments, such as those utilizing machine-learning based models for adjusting facility-specific user data parameters, the IDTS system 400 may modify the facility-specific user data parameters (e.g., as originally generated based at least in part on user-input) to include a wide variety of search parameters. In some embodiments, the IDTS system 400 may generate additional search parameters or keywords based on previously provided search parameters, such that variations of a facility-specific user data parameters are included in a particular search. For instance, if a facility selected parameter or keyword or search term is "peanut allergy," the search configuration application will add variations of the word or conceptually related words, such as "food allergy" or "food preference." As yet another example, a facility selected parameter may be provided as a broad term, such as "allergies," thereby requesting data indicative of any allergies of users entering the facility. In certain embodiments, the IDTS system 400 may be configured to remove one or more parameters from the facility-specific user data parameters, for example, upon determining that the one or more parameters are not sufficiently relevant to the facility characteristics to warrant sharing of the parameters.

As discussed herein, the IDTS system 400 (e.g., portions of the IDTS system 400 operating at the user's user computing entity) may be configured to generate a proposed user dataset comprising user data deemed relevant to satisfying the facility-specific user data parameters in response to the request (e.g., the request generated at and transmitted from the IDTS system 400 portions operating at the facility's user computing entity), and accordingly the IDTS system 400 may be configured to determine, based at least in part on the proposed user dataset that meets the facility-specific user data parameters and the input indicative of the current context of the user or the context of the environment of the user, a relevance score and a sharing eligibility of the proposed user dataset that meets the facility-specific user data parameters.

Although facility-specific user data parameters may be specified based at least in part on user-input, certain embodiments may operate by automatically determining one or more of the facility-specific user data parameters to be associated with a facility profile. For example, in instances in which a facility does not self-define facility-specific user data parameters to be received from users, the IDTS system 400 may be further configured to analyze various data, such as facility characteristic data, facility-specific user data parameters associated with similar facilities (e.g., based on determined similarities between facility characteristic data), and/or the like to determine recommended facility-specific user data parameters to be associated with the facility profile. The recommended facility-specific user data parameters may be automatically implemented upon generation, or the recommended facility-specific user data parameters may be implemented after receipt of approval from a representative associated with the facility.

Similar configurations may be utilized for adjusting previously-specified facility-specific user data parameters. For example, a proposed set of adjusted facility-specific user data parameters is generated (e.g., automatically, based at least in part on machine-learning based configurations) by the IDTS system 400 to favor user data relevant to the facility characteristics over irrelevant user data. In certain embodiments, the prior, previously-specified facility-specific user data parameters comprises data indicative of previously-implemented facility-specific user data parameters. Such data may be analyzed, for example via one or more machine-learning based models, to determine whether parameters are similar to parameters specified by facilities having similar characteristics so as to determine whether such parameters are deemed relevant to a particular facility. Based on analysis of the prior facility-specific user data parameters, the IDTS system 400 may be configured to generate a proposed adjusted set of facility-specific user data parameters to be implemented on behalf of the facility.

In certain embodiments, the IDTS system 400 may support multiple algorithms and methodologies, including those discussed below with respect to analyzing proposed data together with existing and/or learned data to develop a user data model/prediction to generate a recommendation of proposed facility-specific user data parameters to enable a facility to accommodate relevant specific needs of the user. Moreover, the facility-specific user data parameters may evolve over time in accordance with the one or more algorithms and/or methodologies utilized to define the recommendation data, such that facilities obtain increasingly more relevant data from users over time.

Figure 4:
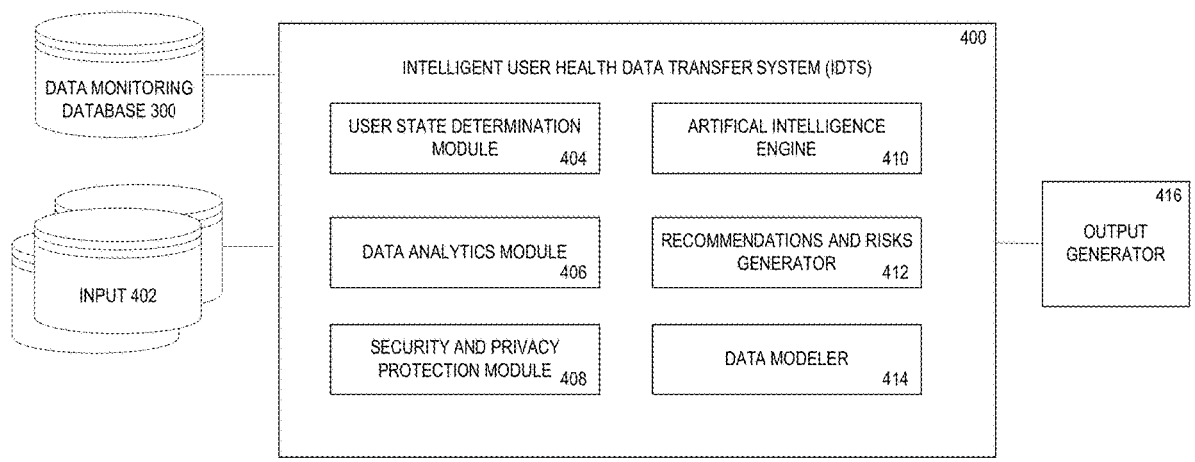
FIG. 4 illustrates an example Intelligent User Health Data Transfer (IDTS) system in accordance with some embodiments discussed herein.

In some embodiments, with reference to FIG. 4, the IDTS system 400 may include a user state determination module 404, a data analytics module 406, a security and privacy protection module 408, an artificial intelligence engine 410, a recommendations and risks generator 412, and a data modeler 414, some or all of which may be in communication with the data monitoring database 300. Moreover, as discussed herein, certain aspects of the IDTS system 400 may be implemented by one or more user computing entities and/or a third party intermediary system. The IDTS system 400 may receive one or more input data indicative of a current context of the user, a current location of a user (e.g., based on an exact location of a user's user computing entity and/or a relative location of the user's user computing entity relative to one or more facilities, as identifiable for example based on potential connectivity between the user's user computing entity and the facility's user computing entity), and/or a context of an environment of the user and may generate the appropriate notifications to selectively and securely share user data with a facility to enable the facility to accommodate specific needs of a user (identifiable based on the user data received by the facility) according to a user data model using artificial intelligence. The IDTS system 400 may use any of the algorithms, operations, steps, and processes disclosed herein for securely sharing user data with a facility to accommodate specific needs of a user.

To provide user data to specific facilities, the IDTS system 400 may receive a plurality of inputs 402 indicative of user data and/or a current context of the user or a context of an environment of the user, for example, from one or more user computing entities 10A-10N. The IDTS system 400 may process the inputs 402 to produce an output via an output generator 416, which may include appropriate notifications, strategies, recommendations, and/or messaging communications to be provided to one or more representatives of the facility to enable the representatives to improve user accommodations (e.g., adaptions and/or alterations that meet the user's specific medical needs). In some embodiments, the IDTS system 400 may execute user state and environment state determination using the user state determination module 404, process the data in the data analytics module 406, provide data security and privacy in the security and privacy protection module 408, train user data models/strategies and/or recommendation models/predictions via the artificial intelligence engine 410, generate the recommendations in the recommendation and risks generator 412, update the user data models/strategies and/or the recommendation models/predictions in the data modeler 414, and output the results via the output generator 416 which may, in turn, be configured to output one or more automated notifications via the communications interface 208 and/or any suitable user computing entities 10A-10N. Each of these steps may obtain data from a plurality of sources including the data monitoring database 300.

When inputs 402 are received by the IDTS system 400, an environment and/or a user state determination using the user state determination module 404 may be made. An environment and/or a user state determination includes such information as the user's historical health data, real-time health data, external conditions (e.g., environmental conditions), and user preferences. This information may give context to the user's environment and the user to determine the environment and user state. For example, the user state determination module 404 may inform the IDTS system 400 as to any health risks and recommended actions to be taken to accommodate the user's specific medical needs.

The IDTS system 400 may generate an output using the data analytics module 406, the security and privacy protection module 408, the artificial intelligence engine 410, the recommendations and risks generator 412, and the data modeler 414. The data analytics module 406 draws information about the applicable profile data, environmental data, user capabilities data, IoT (Internet of Things) data, historical data, sensor data, learned data, recommendation engine data from the data monitoring database 300 and then, in light of the user state determination module's 404 determination, analyzes the data to generate proposed user dataset to be shared securely to a facility to enable the facility to accommodate the specific medical needs (as identified within the provided user data and/or any user preferences provided with the user data) of the user. The data analytics module 406 is configured to predict the user's most likely activity levels over time and to associate the user's activities or context with data from the environment states to better predict relevant user data to be shared with a particular facility. For example, knowing that the user has a food allergy (based on user data provided to a restaurant facility) allows a restaurant facility to adapt a menu to accommodate the user's food allergy. In the event that a particular facility does not self-specify user data to be received, forecasting the specific user data needed by a facility can be achieved in the artificial intelligence engine 410.

In some embodiments, the user's state, for example, may be relevant to the user's historical health data as reflected by electronic health records (e.g., EHR, IHR, etc.), activity level (e.g. from wearable sensors), stress level (e.g. from Galvanic Skin Response wearable sensor), conversation (e.g. from an ambient IoT Virtual Personal Assistant), user preferences (e.g., prefer close to restroom, avoid loud, noisy restaurants, etc.) and/or the like. The state of the environment may include presence of the user within the environment (e.g. proximity of wearable IoT sensor to the home wireless network), the room which the user occupies (e.g. from Passive Infrared sensors), weather conditions, factors leading to allergies (e.g., pollen count), and/or the user's proximity to a restroom (e.g. via detection of iBeacon, Eddystone or other Bluetooth Low Energy by the users personal IoT device).

The security and privacy protection module 408 may be configured to appropriately preserve a user's privacy when sharing user data in accordance with certain embodiments, given a request for such data from a particular facility. In some example embodiments, the security and privacy protection module 408 determines and/or implements security measures (e.g., anonymize user data) based on a rules-based system for implementing particular security measures. However, it should be understood that, where relevant, the security and privacy protection module 408 may be configured to utilize one or more models generated via one or more artificial intelligence and/or machine learning algorithms to ascertain appropriate levels of privacy and/or security for providing user data to a facility user computing entity. In certain embodiments, the artificial intelligence engine 410 may be generated at the IDTS system 400, and/or may be provided to one or more user computing entities 10A-10N for execution and/or updating. It should be understood that the artificial intelligence engine may be utilized for implementing a variety of aspects of certain embodiments, such as determining relevance scores for particular user data, determining appropriate security and privacy considerations for sharing particular user data, and/or the like. The artificial intelligence engine may provide a plurality of algorithms, which may utilize a generative approach, a discriminative approach, "if then else" approach, and/or other approaches for providing training data to the artificial intelligence algorithm.

The recommendations and risks generator 412 may be configured for such reinforcement learning (and/or other types of learning) in which a recommendations model/strategy or facility adjustment plan to accommodate specific needs of the user is generated and sent to the facility, such that the user's medical needs may be appropriately addressed by the facility. For example, the recommendations and risk generator 412 may be configured to determine appropriate actions to be taken by a facility to address specific types of user data. Moreover, in certain embodiments, the recommendations and risks generator 412 may operate in concert with additional modules discussed herein to propose user data needed by a facility based on the type of facility. The recommendations and risks generator 412 can use learning techniques to generate a recommendations model/strategy for the user and/or facility which ensures relevant medical issues of the user are known to the facility and that an adjustment plan is recommended/executed to maximize the user's well-being while at the facility. The recommendations and risks generator 412 may be further configured to communicate any health risks (for example, the probability of occurrence of medical disease). That is, the communicated health risks may include a list of medical conditions or diseases that are likely to develop while at the facility.

Based on the generated recommendation model/strategy, the IDTS system 400 may be configured to determine an appropriate output via the output generator 416, such as presenting one or more control instructions to an IoT device (e.g., lower temperature of room, dim lights, etc.) and/or presenting notifications via the communications circuitry of one or more user computing entities 10A-10N (e.g., provide an facility adjustment having instructions to remove dishes with peanuts from the menu).

As discussed herein, the IDTS system 400 may also determine the proposed user dataset to be generated and sent to a facility based on the type of facility. In such instances, the IDTS system 400 may be configured to determine the appropriate and relevant user data (e.g., food allergies, physical disabilities, user preferences regarding restaurant seating location, and/or the like) to provide to a particular facility (e.g., restaurant). The result of the unique combination of techniques from artificial intelligence and data analysis leads to maximizing the user's well-being while at the facility which can significantly increase quality of life for the user.

As will be appreciated, one or more of the IDTS system 400 components may be located remotely from other components, such as in a distributed system. Furthermore, one or more of the components may be combined and additional components performing functions described herein may be included in the IDTS system 400. Thus, the IDTS system 400 can be adapted to accommodate a variety of needs and circumstances.

IV. Exemplary System Operation

The operation of various embodiments of the present invention will now be described. As discussed herein, various embodiments are directed to systems and methods for selectively and securely sharing user data with a facility to accommodate specific needs of a user.

A. User Registration

Each user or facility may have a profile (e.g., a user profile or a facility profile, as applicable) accessible via the IDTS system 400 and/or stored via one or more user computing entities 10A-10N and/or the IDTS system 400. For example, a user or facility can input various information to register/enroll and create or update a user profile for storage and use by the IDTS system 400 and/or stored via one or more user computing entities 10A-10N. Such profiles can be created, stored, edited, and/or customized manually, automatically, and/or semi-automatically to adapt to various needs and circumstances.

To provide appropriate user data to a facility, the IDTS system 400 (via the one or more user computing entities 10A-10N) is configured to receive and store user profile data 304 for one or more individual users. As discussed herein, the user profile data 304 comprises data indicative of the medical history for the user, sharing preferences of the user (e.g., always share food allergies and hearing impairment, do not share certain diseases), as well as data indicative of a current context of the user or a context of an environment of the user that may be anonymized and provided to a facility. In certain embodiments, the sharing preferences of a user may identify one or more specific facilities with which the user would like to share his/her user data (e.g., identified by business names associated with the facility). In other embodiments, the sharing preferences of a user may identify one or more categories of facilities with which the user would like to share his/her user data (e.g., share with restaurants, share with electronics stores, and/or the like). In yet other embodiments, the sharing preferences of a user may identify a global sharing preference, indicating the user desires to share user data with any requesting facility. In yet other embodiments, the sharing preferences of a user may identify one or more "blacklisted" facilities (e.g., specific facilities, categories of facilities, and/or the like), these blacklisted facilities would not receive user data for the user, however other facilities not falling into the identified blacklist would receive user data for the user. Moreover, the sharing preferences may provide granular control of sharing preferences for the user, for example, a user may identify one or more user data types to share (or not to share) with facilities, and such preferences may apply to specific facilities, to categories of facilities, globally, and/or the like.

The user profile data 304 may comprise additional user-specified data in certain embodiments, such as user preferences (e.g., restaurant seating preferences, grocery shopping cart preferences, store temperature preferences, and/or the like), user identifying data (e.g., height, weight, hair color, eye color, identifying tattoos, one or more photos, and/or the like), and/or the like. In embodiments, the user preferences may further identify one or more specific IoT devices with which the IDTS system 400 is permitted to capture data from (e.g., identified by IoT device name associated with the IoT device).

Moreover, the user profile data 304 may comprise user identifier data, such as a user name, a password, a user's real name, contact information (e.g., phone number, email address, mailing address, and/or the like). Such identifier data may be utilized to synchronize and/or link various devices (e.g., sensor devices, and/or the like) for operation with the user's computing entity, as discussed herein. By linking various devices with a user computing entity and/or a user's profile, the user profile data 304 may be enriched with real-time (or near real-time) data generated by the one or more sensors to be associated with the user. For example, a real-time user's heart rate may be reflected within the user profile data 304 for a user wearing a heart rate monitor. As discussed herein, such real-time data may be shared with a facility, in addition to, or in the alternative to static data such as known health conditions, known user preferences, and/or the like. A facility may include the same identifier data and may be stored in the user profile data 304.

In certain embodiments, the user profile data 304 may additionally comprise real-time data generated for the user, such as real-time data generated by one or more sensors onboard and/or in communication with the user computing entity. For example, the real-time data may comprise real-time health data, such as data indicative of a user's pulse, blood pressure, body temperature, and/or the like. The real-time data of certain embodiments may be further indicative of recent activities of the user (e.g., recent exercise activities, recent eating activities, recent sleeping activities, and/or the like).

In certain embodiments, the profile data 304 for a facility may include data indicative of the facility's type (e.g., restaurant, building, sporting complex, music hall, etc.) and any other data that may distinguish the facility from other facilities of the same type (e.g., vegan restaurant). The profile data 304 for a facility may additionally comprise data indicative of one or more characteristics of the facility (e.g., permanent characteristics of the facility, semi-permanent characteristics of the facility, temporary characteristics of the facility), for example, that may be utilized to identify similar facilities when identifying facility-specific user data parameters for implementation on behalf of the facility and/or when identifying relevancy scores for user data to be provided to the facility user computing entity. As discussed herein, the characteristics of the facility may be indicative of characteristics occurring and/or otherwise under the control of the facility and/or characteristics impacting individuals in and/or proximate the facility (e.g., the facility is located near a sewage treatment plant emitting noxious odors). As indicated, the profile data 304 for a facility may further include facility-specific user data parameters identifying user-data requested by the facility and capable of identifying one or more health conditions of a user (and/or user preferences) that is relevant to the facility such as allergies, vaccinations, immunizations, environmental sensitivities, disabilities, diseases, eating habits, disease susceptibility, stress response, skin disorders, injuries, heart rate or medications taken by the user. For example, as reflected within the facility-specific user data parameters, a restaurant type facility may request information about a user's food allergies while a retail type facility may not request information about a user's food allergies. Moreover, the profile data 304 for a facility may comprise additional facility-specific data, such as data indicative of various facility-specific hazards, characteristics, and/or the like. For example, the profile data 304 for a facility may indicate that the facility has active heavy equipment moving therethrough (e.g., for a home improvement store), the facility is characterized by high noise levels, the facility is characterized as being dimly lit, and/or the like. In embodiments, the profile data 304 of a facility may comprise geographic features (e.g., bodies of water, etc.), or any other suitable known geographic feature that may have an impact on patients' health (e.g., water treatment plant).

Moreover, in certain embodiments the profile data 304 for a facility may be updated to reflect time data, such as accessibility times (e.g., times during which the facility is open to the public) event times (e.g., times during which a public or private event is scheduled to occur), and/or the like. As discussed herein, the time data may be utilized to time-limit when a facility may receive user data from one or more users. As discussed herein, a facility's access to user data may be limited to the time during which an event is scheduled (e.g., upon the conclusion of the event, the user data of one or more users visiting the facility is no longer accessible to the facility), thereby providing additional privacy protection for individuals.

The user profile data 304 for a facility may further comprise additional user-specified data in certain embodiments, such as communication preferences (e.g., communication methods to interact with the user). In embodiments, the communication preferences may identify Short Message Service (SMS), Multimedia Messaging Service (MMS), and the like.

To register a user or a facility, an individual (e.g., the user, a care provider associated with the user, the facility, an owner or employee associated with the facility, and/or the like) may provide identifying information about the user or facility to the IDTS system 400 and/or the one or more user computing entities 10A-10N for storage, for example, in the data monitoring database 300 (which may be stored locally at a corresponding user computing entity and/or within a memory storage area of a third party intermediary system as discussed herein). The identifying information may be provided via an interactive user interface displayed via a user computing entity 10A. The interactive user interface may be configured to accept user input indicative of the profile data 304 for the particular user or facility.

Upon receipt of the user input, the IDTS system 400 may generate a user profile comprising the profile data 304 within the data monitoring database 300 for storing data associated with the user or facility. Moreover, upon generation of a user profile corresponding to a facility, the IDTS system 400 may assign an initial recommendation model/strategy and/or user data model/prediction to the user or facility to be stored in association with the user profile. For example, particularly in embodiments in which a representative of a facility does not specify user data to be requested upon users visiting the facility, the IDTS system 400 may be configured to recommend various facility-specific user data parameters, for example, based at least in part on determined characteristic similarities with other facilities. As discussed herein, the IDTS system 400 may store a plurality of initial recommendation models/strategies and/or user data models/predictions each applicable for different user characteristics and facility types. However, it should be understood that in certain embodiments, the initial facility-specific user data parameters may be generated based at least in part on user-input specifying desired facility-specific user data parameters for a newly generated facility profile. Thus, the IDTS system 400 may be configured to select an initial recommendation model/strategy and/or user data model/prediction to be assigned to the user profile that is most-applicable to the user characteristics or facility type identified within the corresponding profile. As a specific example, upon generation of a facility profile for a sporting complex type facility, the IDTS system 400 may be configured to select an initial recommendation model/strategy and/or user data model/prediction for requiring facility-specific user data parameters related to environmental sensitivities and disabilities so as to implement a facility adjustment plan to provide curbside wheelchair service and the like.

In certain embodiments, the recommendation model/strategy may be generated to provide a facility adjustment plan to a facility so as to enable the facility to better accommodate a user's specific medical needs (or a user's provided preferences). The recommendation model/strategy may comprise data identifying various actions items (that may be manually implemented by representatives of the facility or automatically implemented by the facility user computing entity interacting with various computing-related systems of the facility) that may be performed to address corresponding user data types. For example, the recommendation model/strategy may indicate that user data identifying a preference for cooler-temperature seating within a restaurant may correlate with a recommended action item of seating the corresponding user under an air vent (or within specified seats within the facility). As another example, the recommendation model/strategy may indicate that user data identifying a user's peanut allergy may correlate with a recommended action item of providing the user with an allergyfriendly menu to avoid peanut exposure. As yet another example, the recommendation model/strategy may indicate that, upon receiving data specifying a noise sensitivity of a user entering the facility, the facility's user computing entity may provide executable instructions to a network-enabled sound system of the facility to automatically lower the output volume of the sound system. The user data model/prediction may be generated to provide proposed facility specific user data parameters for a particular type of facility in the case where the facility has not already established a set of facility-specific user data parameters. In certain embodiments, the initial recommendation models/strategies and/or user data models/predictions stored via the IDTS system 400 may be continuously evolving (e.g., through machine learning based at least in part on data generated by each of a plurality of individual users and facilities).

With reference again to the registration process, the IDTS system 400 may be configured to receive data indicative of one or more devices associated with the user. In certain embodiments, the IDTS system 400 may automatically generate and/or store data indicative of the various devices associated with the user, in response to log-in requests for the user received from various devices. For example, users may download and install software applications on one or more electronic devices (e.g., computers, mobile devices, wearable computing entities, and/or the like), and may provide identifying information (e.g., log-in credentials) via a user interface provided through the installed software program on each of the user computing entities. Upon logging into the software program on each of the user computing entities, the IDTS system 400 may be configured to collect device data regarding each device providing the user identifying data and may store the device data in association with the user profile. In certain embodiments, the device data may comprise device identifying data (e.g., IP address, MAC address, device name, and/or the like), and/or device capabilities data. The device capabilities data may be indicative of whether the device is usable for providing automated notifications (e.g., alert notifications) received from a user computing entity 10A, for generating sensor data (e.g., indicative of user and/or environmental data), and/or the like.

In certain embodiments, device data may further be provided manually and/or via interactions with other computing systems. For example, a user may provide device identifying data (e.g., an IP address) for a plurality of IoT devices (e.g., thermostats, proximity sensors, flowmeters, and/or the like) to be associated with the user profile and for providing sensor data for the user profile. As yet another example, the IDTS system 400 may be in communication with other, external systems, such as a thermostat monitoring system (e.g., central servers associated with one or more IoT enabled thermostats), and accordingly the IDTS system 400 may be configured to automatically request and/or retrieve device identifying data for each of one or more devices from the external system.

Once a user or facility is registered, the IDTS system 400, via one or more user computing entities 10A-10N, may be configured to generate notifications via one or more registered devices for the user or facility and/or to receive sensor data, medical data, and/or context data from the one or more user computing entities.

B. User Location Monitoring

In embodiments, GPS satellites operate to determine the geographic location of a user computing entity 10 associated with a user. The computing entity receives GPS signals and determines its location. For purposes of illustration and without limitation, this may occur solely through using the GPS system, or may occur by using a filter to combine location data from the GPS system and another system such as cell-tower-triangulation in order to obtain a more accurate location.

In some embodiments, the IDTS system 400 periodically receives and stores geographic location information associated with the computing entity. The information is sent from the computing entity; however, it may also be pulled from the computing entity, or obtained from another service that is able to determine the location of the mobile device. The information includes not only geographic location data, but also the speed and the direction of the computing entity.

In some embodiment, facilities may provide Wi-Fi access points accessible to users (e.g., open networks or password accessible networks). These access points which are registered to the IDTS system 400 may also be used to locate the user. For example, upon determining that a particular user computing entity 10 is connected to a Wi-Fi access point, the physical location of the user computing entity 10 may be determined to be within a known range of Wi-Fi signal provided by the access point (and thus the user computing entity 10 may be determined to be proximate to a particular facility simply based on the user computing entity 10 being connected with a Wi-Fi access point located at the facility. The IDTS system 400 may then analyze the computing entity's IP address information to determine the facility the user (determined via proxy based on the location of the user's user computing entity 10) is currently located at. Alternatively, the IDTS system 400 can use ambient Wi-Fi information in order to determine the user computing entity's location. In certain embodiments, the range of a particular Wi-Fi access point may be correlated with geographic coordinates (e.g., the boundaries of the Wi-Fi access point range may have corresponding longitude/latitude coordinates corresponding to a range-boundary). However, certain embodiments need not include such level of detail, as determining that a user computing entity 10 is within range of a Wi-Fi access point may provide sufficient precision regarding the location of the user (and the user computing entity 10) for functionality as discussed herein. In some embodiments, a Bluetooth Low Energy (BLE) beacon may be configured to broadcast a signal comprising data indicative of the BLE beacon's coordinates, and this signal can be detected by a mobile device (e.g., a user computing entity), and such coordinates may be utilized for providing additional detail regarding the current location of the user computing entity 10. For example, to determine the current location of the user computing entity 10, the user computing entity 10 can receive a broadcast signal from the beacon that comprises data indicative of the location of the beacon. Because the user computing entity 10 receives data broadcast directly from the beacon (indicating the user computing entity 10 is in close proximity to the beacon), the user computing entity 10 may estimate its own location to be the location of the beacon. Moreover, the beacon may be configured to advertise location based services provided via a beacon network. For example, upon determining that the user computing entity 10 crossed a geographic region defined by the beacon network, the user computing entity 10 may receive this information via a signal from the beacon network.

The geographic location information describing various facility locations are stored by the IDTS system and such facility location information may be transmitted to the computing entity when the geographic location of the computing entity is located in proximity to the geographic location of the facility (e.g., within the perimeter of the facility location). In some embodiments, the user is permitted to disable the monitored location information.

In embodiments, the computing entity is notified by the IDTS system 400 that the user is in proximity to a facility. The IDTS system 400 may then transmit information about the facility to the computing entity. In some cases, the IDTS system 400 may only transmit facility information to the user's user computing entity when the geographic location of the computing entity corresponds to the geographic location of the facility or the geographic location of the facility is in proximity to the geographic location of the computing entity. In certain embodiments, transmitting data indicative of the facility to the user's user computing entity may comprise transmitting data indicative of requested user data from the facility, thereby enabling the user to determine whether to accept the data request and enable transmission of the user data to the facility's user computing entity. In certain embodiments, enabling the user to selectively enable data transmission may comprise providing a user display of the data types requested by the facility (although the user cannot see corresponding values to be transmitted for each of the plurality of data types requested).

Once the IDTS system 400 transmits a notification to the user computing entity 10 of the facility in proximity to the geographic location of the computing entity, the user's user computing entity may transmit a notification to the facility that the user is about to enter the facility. Additionally or alternatively, the IDTS system 400 may transmit the notification to the facility that the user is about to enter the facility. In response, the facility may transmit a request for user data associated with the user of the computing entity that is applicable to the facility, wherein the request identifies facility-specific user data parameters corresponding to characteristics of the user as reflected by at least a portion of the user data.

C. Facility-Specific User Data Parameters

Figure 5:
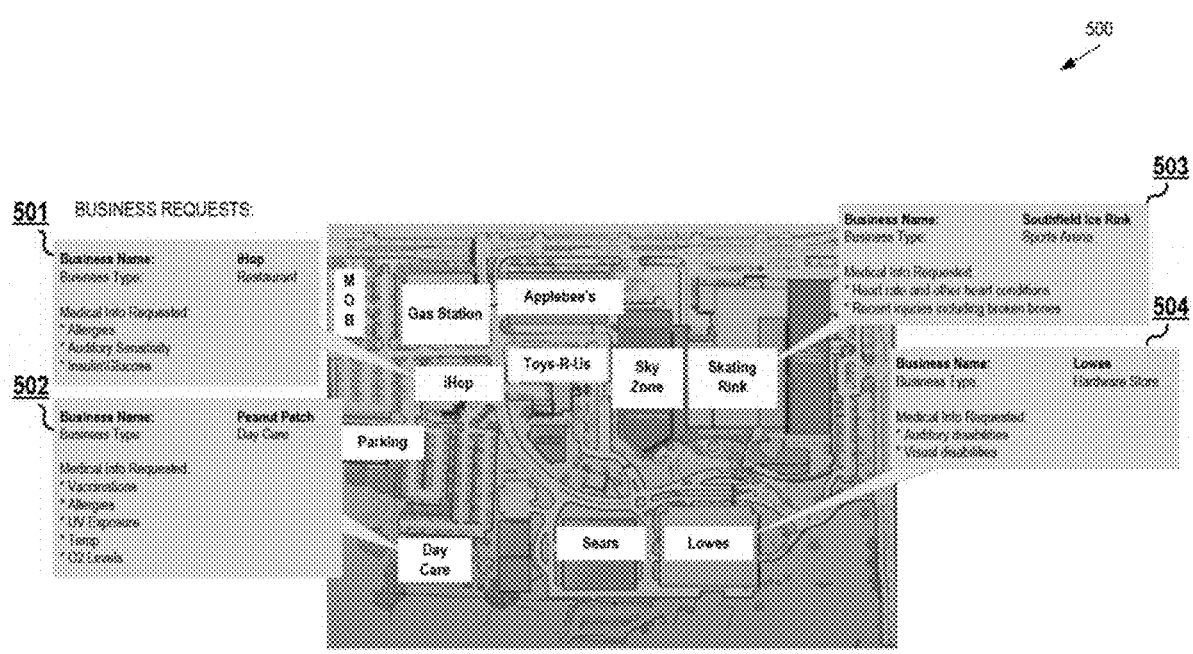
FIG. 5 illustrates example user medical information requested by different business using the IDTS system in accordance with some embodiments discussed herein.

In embodiments, the facility (via the facility user computing entity) identifies facility-specific user data parameters corresponding to characteristics of the user for which the facility desires information as reflected by at least a portion of the user data (e.g., a set of key words to locate relevant user characteristics and/or user data). The facility-specific user data parameters are included as part of a request for user data (e.g., transmitted to a user's user computing entity when the user's user computing entity is within a designated range of the facility), and reflect desired user data to be received by the facility. In an example embodiment, the IDTS system 400 (e.g., aspects of the IDTS system 400 implemented at the user's user computing entity) may examine the facility-specific user data parameters to identify user data (e.g., indicative of specific characteristics of the user) that satisfy the criteria set forth by the facility-specific user data parameters. For example, if the request from the facility user computing entity requests allergy information of users proximate/within the corresponding facility, then the IDTS system 400 looks for user data identifying user characteristics indicating any allergies. In certain embodiments, the user data may be structured with corresponding metadata identifying data types (e.g., metadata associated with specific items of data identifying those items of data as allergy-related), and accordingly identifying allergy-related data may comprise identifying user data tagged as being allergy data. In other embodiments, the user data may be unstructured, and accordingly identifying relevant data may comprise parsing the user data (e.g., via natural language processing systems and/or language identification models) to identify relevant user data to be provided in response to a user data request from a facility user computing entity. In an example embodiment, the IDTS system 400 may generate one or more queries to a data monitoring database 300 to locate potential user data associated with the facility-specific user data parameters. The IDTS system 400 may then identify keywords in the potential user data and match the identified keywords with a predetermined list of keywords, wherein the predetermined list of keywords comprises a list of most frequently used keywords to describe the facility-specific user data parameters, wherein the potential user data is added as the proposed user dataset when determining that the identified keywords match the predetermined list of keywords. FIG. 5 illustrates example facility-specific user data parameters.

FIG. 5 provides an illustration 500 of various example facility requests 501, 502, 503, and 504 associated with specific facilities. Referring now to facility 501, the facility is a restaurant with facility-specific user data parameters comprising allergies, auditory sensitivity, and insulin/glucose data. Facility 502 is a day care type facility requesting different facility-specific user data parameters from facility 501. Facility 503 is a sports arena requesting different facility-specific user data parameters from facilities 501 and 502. Facility 503 requests medical information from the IDTS system 400 related to a user's heart rate and other heart conditions, and any recent injuries including broken bones. Finally, facility 504 of FIG. 5 illustrates a hardware store type facility requesting medical information of a user related to auditory disabilities and visual disabilities. Using a graphical user interface (GUI), the user may be alerted to specific user data requested by each facility.

In some embodiments, the facility may not identify facility-specific user data parameters, and as such the IDTS system 400 may access, from a data monitoring database 300, the user's prior proposed user dataset set in response to a prior data request from a facility having a facility type corresponding to the facility's facility type. The IDTS system 400 may then analyze the prior proposed user dataset set and the proposed user dataset set using a set of analysis rules to generate a recommendation. The recommendation provides proposed facility-specific user data parameters corresponding to characteristics of the user as reflected by at least a portion of the user data.

In some embodiments, the IDTS system access a reference table (e.g., stored within and accessible via a memory storage area) to determine appropriate user data to be provided to the facility. The reference table may comprise data identifying predetermined user data matching facility-specific user data parameters. For example, the table may establish that for a facility requesting data type A (e.g., data related to allergies or light sensitivity), the IDTS system 400 is configured to automatically transmit in response to the request a user dataset comprising identifying a gluten allergy and no light sensitivity. In this example embodiment, the IDTS system performs the reference table lookup to find data type A. If an exact match is found in the user profile data 304, the IDTS system is configured to provide the predetermined user dataset to the facility. However, if an exact match is not found (e.g., no data type A), the IDTS system 400 may be configured to refrain from transmitting user data to the facility. In other embodiments, other data matching other data facility-specific user data parameters may be transmitted to the facility.

D. User Data Monitoring and Data Collection

Figure 6:
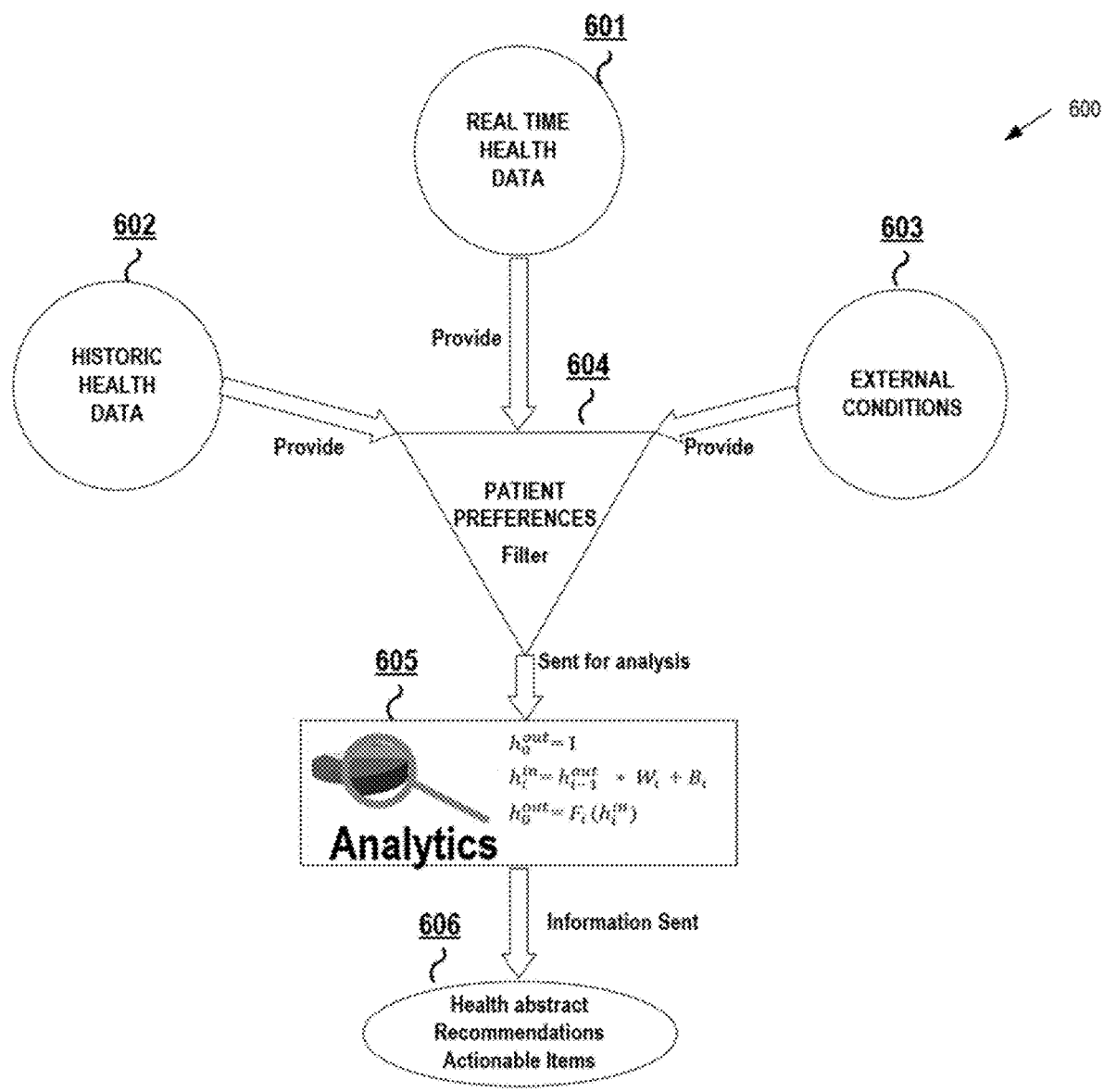
FIG. 6 illustrates an example high level architecture of a system in accordance with some embodiments discussed herein.

FIG. 6 specifically illustrates an example high level architecture of the IDTS system 400 providing various operations, steps and processes for monitoring user and/or environmental characteristics (e.g., environmental context data) for a particular user, via the IDTS system 400 and/or the one or user computing entities 10A-10N or other user-specific devices. As discussed throughout this description, embodiments may be implemented in an environment in which aspects of the IDTS system 400 are executed via the user's user computing entity and the facility's user computing entity. In other embodiments, embodiments may be implemented in accordance with a third-party intermediary system executing the functionality of the IDTS system 400. Via the various steps of FIG. 6, a facility adjustment plan may be generated and transmitted to a facility. Such facility adjustment plan may include instructing the facility to provide one or more accommodations for various users, such as providing curbside wheelchair assistance, instructing the facility to provide a dairy-free menu, controlling various automation systems at the facility, such as to adjust the lighting and/or temperature of the facility, positioning emergency responders within a particular region of the facility, and/or the like.

As indicated at circles 601, 602, and 603, of FIG. 6, the IDTS system 400 and/or various user computing entities 10A-10N collect data from health records, various sensors, monitoring user characteristics (e.g., user context data), monitoring environmental characteristics (e.g., environmental context data), and/or the like to compile user data.

Historical heath data 602 of the user data may include data obtained from electronic health records (EHR), sometimes known as electronic medical record (EMR), which is a collection of electronically stored information about a user's lifetime health status and health care. EHRs may include a broad range of data, including demographics, medical history, medication and allergies, immunization status, laboratory test results, radiology images, vital signs, personal statistics like age and weight, and billing information. Many EHR systems combine data from a number of health care services and providers, such as clinical care facilities, laboratories, radiology providers, and pharmacies.

To retrieve this information, the IDTS system 400 (e.g., of a third party intermediary system and/or the user's user computing entity) may send a request for user medical information to an EHR system using one or more application programming interface (API) calls. In response, the EHR system may retrieve the user medical information from an EHR medical records database and return the user medical information to the IDTS system 400 via network 20. In embodiments, the IDTS system 400 may request access to the EHR system's APIs beforehand to ensure that the API requests from the IDTS system are valid and authorized.

Real-time health data 601 may further include user data collected from IoT devices including wearable devices with multiple sensors with the capability of collecting biological or physical data (e.g. heart rate, blood oxygen and sugar levels, body temperature, etc.). The wearable device may also be used to determine the physical or mental status of the user over time. Moreover, wearable device sensors can also monitor and collect data on the environment (location, altitude, air pollution, distance traveled, external temperature, etc.) surrounding the user of the wearable device.

External conditions 603 may include real time environmental information measured by a group of sensors of the user's computing entity or through software applications on the user's computing entity used to communicate to the IDTS system 400 the user's environmental data including measured values of temperature, weather, pollen count, traffic conditions, and the like.

In some embodiments, data is collected constantly over time. Additionally or alternatively, data is collected only when the user is within proximity to a facility (e.g., determined based at least in part on location data generated by the user's user computing entity, based on a determined network connection between the user's user computing entity and the facility's user computing entity, and/or the like) in anticipation the user will enter the facility. In some embodiments, data is collected only when the IDTS system 400 receives a request for user data from a facility. In certain embodiments, the data from circles 601, 602, and 603, may be provided and/or stored at a highly-generic level to preserve a high degree of user privacy. In other embodiments, such data may be collected and stored to provide additional data that may be utilized to develop trends and/or characteristics of the user. As a specific example, if a user always begins their day with a 1-hour workout, the IDTS system 400 and/or the one or more user computing entities 10A-10N may be configured to determine that the user will likely have an high heart rate and sweat profusely for approximately 30 minutes after the workout and as such, the IDTS system 400 will not factor in this high heart rate when the user reaches a retail shopping mall so as to avoid misinterpretations of the user's medical condition by the retail shopping mall. Such data may additionally be determined in real-time (e.g., so as to identify non-scheduled exercise), such that periods of exercise may be identified as they occur, so as to provide additional context regarding the user data when/if provided to a facility.

The IDTS system 400 and/or the one or more user computing entities 10A-10N may be configured to detect any of a variety of user data (e.g., user context data) and/or environmental characteristics (e.g., environment context data) to be associated with a user (e.g., by associating the data with a user profile). As discussed in greater detail in reference to triangle 604, the IDTS system 400 is configured to further filter the user data and environmental characteristics based on the user's preferences (as reflected within the user profile). For example, the IDTS system 400 may be instructed to anonymize the user data to derive an anonymized user data prior to transmitting the same to a facility (e.g., based at least in part on user preferences, privacy-related data, and/or the like). In another example embodiment, the IDTS system may be instructed to implement a time delay between detection of the user at a particular facility and transmitting relevant user data to the facility so as to mask the identity of the anonymized user data such that upon the user entering the facility (e.g., based at least in part on user preferences, privacy-related data, and/or the like), the facility does not determine that the anonymized data is associated with the user. In yet another example embodiment, the IDTS system 400 may send a visual or audible notification to the user via the user's computing entity 10A alerting the user that their user data will be transmitted to the facility. In response to the notification, the user may approve or deny the sharing of their data to the facility. Over time, the IDTS system 400 may be updated to determine whether particular user data may be shared, anonymized before sharing, or not shared at all.

As discussed above, the facility-specific user data parameters may be generated and/or modified based at least in part on models (e.g., machine-learning based models) for identifying relevant data to be requested by a facility, thereby ensuring that facilities only request data relevant for the facility, and to minimize potential intrusion into a particular user's privacy.

As indicated at Block 605 of FIG. 6, with the user data, such as the user historical health data 602, the real-time health data 601, and/or the external conditions data 603, the IDTS system 400 and/or the one or more user computing entities 10A-10N may analyze such data that is further filtered based on the user's preferences to determine an output 606 comprising a health abstract, recommendations, and/or data indicative of recommended actionable items for the facility user computing entity. The output 606 may provide information for a facility to better accommodate specific medical needs of the user.

E. Data Analysis

As illustrated in FIG. 6, the IDTS system 400 may be further configured to analyze the collected data indicative of a current context of the user or a context of an environment of the user to generate a proposed user dataset set to be utilized to populate a health abstract to be provided to the facility user computing entity in response to the facility request for user data. As discussed herein, such a request for user data may be generated in response to a determination that a user is proximate a facility location (based on a determined location of a user computing entity being proximate the facility location as discussed herein). When generating a responsive communication including user data, the IDTS system 400 may configured for executing a two-part analysis to determine a relevance score of the proposed user dataset set and a sharing eligibility of the proposed user dataset set to determine whether each individual item of data is to be included within the health abstract provided to the facility user computing entity. Only data deemed sufficiently relevant (e.g., by satisfying applicable relevance criteria) may be included within a health abstract provided to the facility user computing entity in response to a request for user data.

The relevance score is based at least in part on a relevancy of the proposed dataset to be included within a health abstract to the facility-specific user data parameters, as well as any additional contextual data (e.g., such as user data that would not otherwise be included within the health abstract) applicable to a user, wherein the relevancy is a degree of match to the one or more facility-specific user data parameters. The relevancy score may be rule-based or may be implemented via a machine-learning based model for determining relevance scores for particular items of data. In some embodiments, the IDTS system 400 comprises a set of if-then-else rules. If certain conditions are true, then particular actions are recommended or conclusions are reached. Such a model may be supplemented and/or replaced after a period of time, for example, after a sufficient amount of data is generated for a particular facility to support training data for generation of a facility-specific machine-learning based model for developing relevance scores. In yet other embodiments, a machine-learning based relevance score may be initially borrowed from a different facility location (e.g., such relevance score algorithm being selected based at least in part on a determined similarity between characteristics of the various facilities. For example, each potential user data item of the proposed user dataset set is assigned an initial relevance score of 0. If the potential user data item relates to any of the facility-specific user data parameters, the relevance score is increased to 1. If the potential user data does not relate to any of the facility-specific user data parameters, the relevance score remains as a score of 0. In some embodiments, the potential user data may be added to the proposed user dataset set if its corresponding relevance score exceeds a predetermined threshold. For example, if the relevance score exceeds 3, the potential user data can be added to the set of proposed user dataset that is shared with the facility.

It should be understood that relevance scoring may comprise additional complexities to determine whether a particular item of data that is otherwise relevant to facility-specific user data parameters is determined to be misleading and/or otherwise irrelevant under the specific circumstances of a particular user entering a facility. For example, upon determining that a user's heart-rate is a data type corresponding to facility-specific user data parameters, a simplified relevance scoring methodology may determine that such data is to be shared with the facility user computing entity. However, additional contextual data may indicate that the user's heartrate is elevated likely due to recent exercise, and data indicative of an elevated heartrate should not be conveyed to the facility user computing entity, since such data is not indicative of a particular health condition, but is instead indicative of a user's recent exercise activities, which do not require any specific care on the part of the facility.

Accordingly, a model of generating relevance scores for particular items of data to be included within a proposed dataset of a health abstract may comprise various considerations of data to be included within the health abstract as well as additional user-specific data that would not otherwise be included within the health abstract. Moreover, the models may be developed overtime, for example to reflect the interrelatedness of various user data types. For example, the models may be developed such that particular items of health-related data are indicated as being dependent on recent activities of the user (e.g., identified based on real-time generated user data), and the relevance of such user data may be dependent on whether any recent activities have occurred that would impact the healthcare related data items.

Moreover, sharing of data may be further limited based on the user's sharing preferences identifying whether particular data is eligible for data transmission. The IDTS system 400 may apply a default sharing option to have no user data shared to the facility. In this case, the IDTS system must transmit for presentation the proposed user dataset to a display of the computing entity which is associated with the user and enable the user to approve or deny the sharing eligibility of the proposed user dataset. The user may thus specify when, and/or what types of data may be shared in accordance with various embodiments. Such user preferences may specify particular facilities that have explicit user approval to receive user data, specific data types that the user has approved transmission to various facility user computing entities, specific times when data transmission is explicitly deemed acceptable, and/or the like.

Over time, the IDTS system 400 and/or the one or more user computing entities 10A-10N may determine whether additional user data should be specified/requested within the facility-specific user data parameters, for example based at least in part on the facility type and/or other characteristics of the facility, and based on data requested by other. For example, the IDTS system 400 may access, from a data monitoring database 300, data indicative of user data provided to various facilities of a particular facility type corresponding to the facility's facility type and analyze the prior provided user dataset and the facility-specific user data parameters of a particular facility using a set of analysis rules to generate a recommendation, which provides proposed facility-specific user data parameters to enable the facility to better accommodate the specific needs of a user. In certain embodiments, the analysis rules may be based at least in part on the two-part relevance score and sharing eligibility tests. The prior user datasets provided to various facilities, the proposed facility-specific user data parameters, and/or input indicative of the current context of the user or the context of the environment of the user may be used to train a user data model using machine learning, wherein the user data model outputs the recommendation. However, it should be understood that in other embodiments, the faculty-specific user data parameters may be modified based on user input, without reference to any machine-learning or other automated models.

The IDTS system 400 and/or the one or more user computing entities 10A-10N may continue to modify the recommendations over time. Ultimately, the IDTS system 400 and/or the one or more user computing entities 10A-10N may be configured to generate automated recommendations, facility adjustment plans, proposed user datasets to be shared to a facility, and/or facility-specific user data parameters to maximize the well-being of the user while at the facility.

F. Exemplary Process Flow

Figure 7:
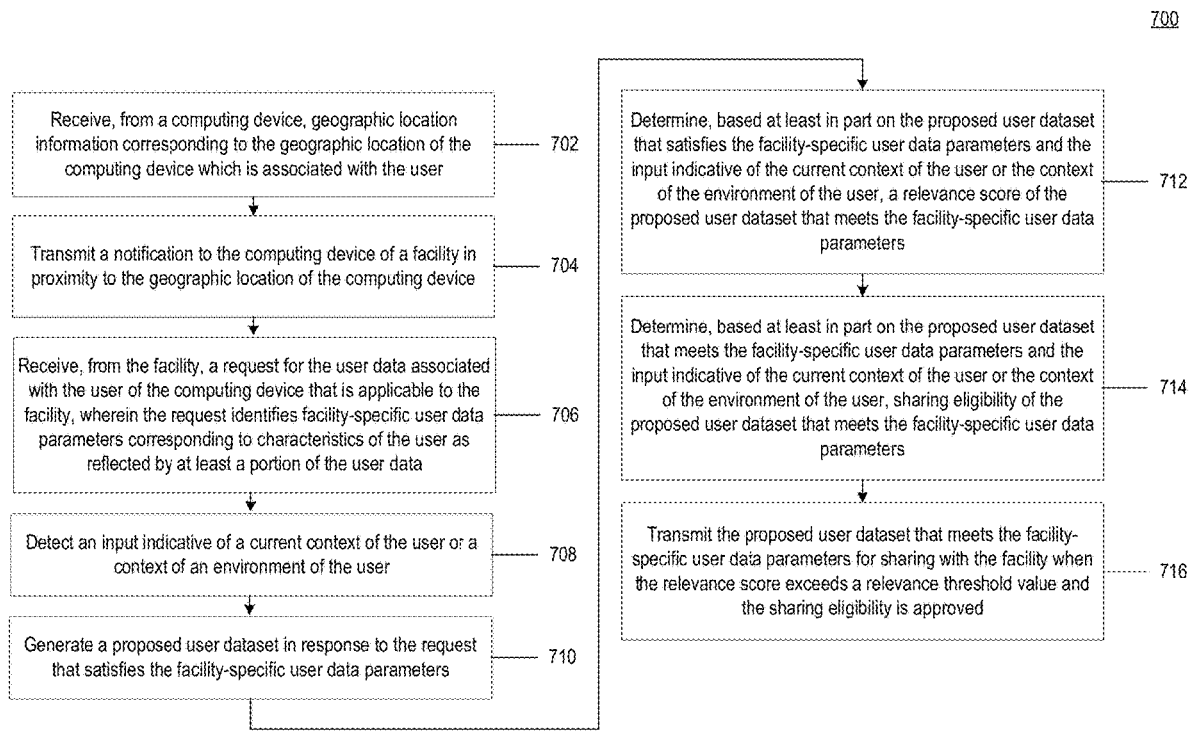
FIG. 7 illustrates a flow diagram of an example IDTS system in accordance with some embodiments discussed herein.

FIG. 7 illustrates a flow diagram of an example system in accordance with some embodiments discussed herein. The method 700 illustrated in FIG. 7 includes steps to receive, from a computing entity, geographic location information corresponding to the geographic location of the computing entity which is associated with the user as indicated at Block 702 and transmit a notification to the computing entity of a facility in proximity to the geographic location of the user computing entity as indicated at Block 704. The notification transmitted to the computing entity may include information about the facility including the facility name, facility type (e.g., restaurant, retail, sporting venue, recreation center, etc.), facility address, facility contact information, facility website information, facility open business hours, and the like. As shown in Block 706, the method further comprises receiving, from the facility, a request for the user data associated with the user of the computing entity that is applicable to the facility, wherein the request identifies facility-specific user data parameters corresponding to characteristics of the user as reflected by at least a portion of the user data.

The method 700 further comprises a step to detect an input indicative of a current context of the user or a context of an environment of the Block 708. The IDTS system 400 and/or the one or more user computing entities 10A-10N may be configured to detect any of a variety of user (e.g., user context data) and/or environmental characteristics (e.g., environment context data) to be associated with a user. For example, the IDTS system 400 and/or the one or more user computing entities 10A-10N may determine that various sensors may be configured to detect user characteristics (e.g., user context data), such as heart rate, perspiration, motion, activities such as eating, drinking, exercising, sitting, standing, and/or the like. Various sensors and applications on the user's computing entity may also detect a plurality of environmental characteristics (e.g., environmental context data), such as weather conditions, pollen count, traffic conditions, proximity to other users, and/or the like.

As indicated at Block 710 of FIG. 7, the suggestion system 214 may generate a proposed user dataset in response to the request that satisfies the facility-specific user data parameters. The proposed user dataset that meet the facility-specific user data parameters are capable of identifying one or more health conditions of the user such as allergies, vaccinations, immunizations, environmental sensitivities, disabilities, diseases, eating habits, disease susceptibility, stress response, skin disorders, injuries, heart rate or medications taken by the user. In some embodiments, generating the proposed user data in response to the request further comprises generating queries to a data monitoring database to locate potential user data associated with the facility-specific user data parameters, identifying keywords in the potential user data and matching the identified keywords with a predetermined list of keywords. In some embodiments, the predetermined list of keywords comprises a list of most frequently used keywords to describe the facility-specific user data parameters, wherein the potential user data is added as the proposed user dataset when determining that the identified keywords match the predetermined list of keywords.

In Block 712, method 700 further comprises determining, based at least in part on the proposed user dataset that satisfies the facility-specific user data parameters and the input indicative of the current context of the user or the context of the environment of the user, a relevance score of the proposed user dataset that meets the facility-specific user data parameters. In some embodiments the relevance score is based at least in part on a relevancy of the proposed data to the facility-specific user data parameters, wherein the relevancy is a degree of match to the one or more facility-specific user data parameters.

In Block 714, the method 700 further comprises determining, based at least in part on the proposed user dataset that meets the facility-specific user data parameters and the input indicative of the current context of the user or the context of the environment of the user, sharing eligibility of the proposed user dataset that meets the facility-specific user data parameters. In some embodiments, determining the sharing eligibility of the proposed user data further comprises transmitting for presentation the proposed user data to a display of the computing entity which is associated with the user and enabling the user to approve or deny the sharing eligibility of the proposed user data. Additionally or alternatively, the sharing eligibility may be preset by the user such that certain user data (e.g., food allergies) are always shared without explicit approval from the user and other data (e.g., psychological diseases) are never shared without explicit approval from the user.

Accordingly, and as shown in Block 716, the method may be further configured to transmit the proposed user dataset that meets the facility-specific user data parameters for sharing with the facility when the relevance score exceeds a relevance threshold value and the sharing eligibility is approved. In some embodiments, the method may be further configured to prior to transmitting the proposed user data that meets the facility-specific user data parameters for sharing with the facility, anonymize the proposed user data that meets the facility-specific user data parameters to derive an anonymized user data and transmit the anonymized user data for sharing with the facility.

In some embodiments, the IDTS system 400 is further configured to determine, based at least in part on the proposed user data that meets the facility-specific user data parameters for sharing with the facility, a facility adjustment plan to accommodate specific needs of the user and transmit the facility adjustment plan to the facility. For example, the facility adjustment plan may include instructions for the facility to provide a vegan, plant-based menu or include controls to dim the lights in the seating area of the user. Several example user cases are described in detail below.

G. Exemplary Use Cases

There are several use cases for the embodiments described herein. For example, a user may attend a large sporting event type facility (e.g., as a spectator of a sporting event). In this example use case, the venue staff of the large sporting event may be alerted of the presence of a user with elevated heart risk. For example, the IDTS system 400 collects user data which indicates that the user has a heart condition, that the user has had an abnormal heart rate within the past 24 hours, and that the external conditions of the sporting event includes a large crowd, high temperatures, and humidity. The IDTS system 400 may further determine that the user prefers not to share information about their psychological condition. Based on this information collected and the preferences set by the user, the IDTS system 400 may analyze this information, implement the two-part relevancy and sharing eligibility tests as described above and provide a recommendation to the venue staff of the large sporting event to be on alert that there is a user seated in section A of the event with a heart condition and that emergency assistance may be needed. With this recommendation, the venue staff may relocate their emergency personnel closer to section A. It should be understood that in such embodiments, the user may elect to share the user data anonymously, as the event venue need only know a general section where the user is located to relocate emergency personnel, such that the emergency personnel are located nearby to the user, just in case the user has an issue. The emergency personnel need not know the identity of the user unless and until the user has heart problems while at the venue, and in such circumstances, the user and nearby spectators can be assumed to point out the identity of the individual needing medical attention. Moreover, it should be understood that in certain embodiments, to maintain the user's privacy, medical data regarding the user's heart condition may be shared after the elapsing of a time delay (e.g., 30 seconds, 2 minutes, and/or the like) after the user is determined to be in proximity to the event venue, such that venue personnel cannot easily correlate the received medical data with the identity of individuals entering the venue. Such data may still be provided with respect to a general location of the user (e.g., the user's seating section) to enable event venue personnel to locate emergency personnel nearby, however such data may be provided so as to avoid unnecessary correlation of the identity of the user with the user's medical condition, if such medical information does not become important during the course of the event. However, it should also be understood that in certain embodiments, the identity of the user may be shared together with the medical data, thereby enabling emergency personnel to quickly identify an individual who may need medical assistance during an event.

Moreover, it should be understood that in embodiments as discussed above in which a user is attending a sporting venue as a spectator of a sporting event, the sharing of user data may be time limited, such that the user's information is only shared during the time period that a sporting event is occurring (and/or shortly before and after the sporting event). In this way, the event venue does not have access to the user's information during time periods in which the venue does not need such information. Such time-based limitations may be implemented by utilizing one or more times for initializing and/or stopping the sharing of user data with a facility. The IDTS system may compare a current time against the times for initializing and/or stopping the sharing of user data before determining whether user data should be shared with a facility. If the current time falls within a period of time during which user data transmission is deemed acceptable, the IDTS system may share the user's data with the venue. However, if the current time does not fall within a period of time during which user data transmission is deemed acceptable, the IDTS system may not share the user's data with the venue.

In another example use case, three users may enter a new restaurant. The first user has a peanut allergy, the second user has hypertension, and the third user has type 2 diabetes. The IDTS system 400 may be configured to share the first user's peanut allergy with the restaurant with a recommendation to seat the group away from the kitchen. The IDTS system 400 may be configured to not send any information about the second user's hypertension condition and with regards to the third user, the IDTS system may provide information to the restaurant that the user has type 2 diabetes with a postprandial blood sugar of 185 mg/dL with a recommendation to present a menu with low carbohydrates and high plant-based options. Based on the IDTS system's recommendation, the restaurant may assign the group a table away from the kitchen, alert the kitchen staff that someone in the group is allergic to peanuts, and present the plant-based menu to the group. In some embodiments, the IDTS system may continue to monitor the three users' health condition in case the first user's peanut allergy is triggered, the second user's blood pressure becomes abnormal, and/or the third user's blood sugar levels become elevated.

In yet another example use case, a user may enter a convenience store. The convenience store may request from the IDTS system facility-specific user data parameters related to heart rate and other heart conditions of the user. A user who just ran at a nearby park may enter the convenience store to which the IDTS system determines not to send information on the user's high heart rate because based on the user's most recent exercise activity and the user's prior user data, the user's current high heart rate is not relevant to the current context of the user and sharing such information may cause misinterpretation by the convenience store staff.

CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. An apparatus configured to selectively and securely share user data, the apparatus comprising at least one processor and at least one memory including computer program code for one or more programs, the at least one memory and the computer program code configured to, with the at least one processor, cause the apparatus to perform at least the following:

receive location information corresponding to the location of a user computing entity associated with a user;

responsive to determining that the location information indicates the location of the user computing entity as being within a proximity distance of a facility, generate, in association with a facility computing entity associated with the facility, a request for user data associated with the user of the user computing entity that is applicable to the facility, wherein the request comprises facility-specific user data parameters corresponding to characteristics of the user as indicated by at least a portion of the user data;

in response to receiving a response to the request that satisfies the facility-specific user data parameters, generate a proposed user dataset;

determine, based at least in part on the proposed user dataset that satisfies the facility-specific user data parameters and additional user data indicative of a current context of the user, a relevance score of the proposed user dataset that satisfies the facility-specific user data parameters;

determine, based at least in part on user-specified eligibility criteria, sharing eligibility of the proposed user dataset that meets the facility-specific user data parameters;

determine, based at least in part on the proposed user dataset that satisfies the facility-specific user data parameters for sharing with the facility, a facility adjustment plan to accommodate specific needs of the user; and responsive to determining that the relevance score satisfies applicable relevance criteria and the user specified eligibility criteria, transmit the proposed user dataset and the facility adjustment plan.

2. The apparatus of claim 1, wherein the at least one memory and the computer program code are further configured to, with the at least one processor, cause the apparatus to perform at least the following:

prior to transmitting the proposed user dataset that meets the facility-specific user data parameters for sharing with the facility, anonymize the proposed user dataset that satisfies the facility-specific user data parameters to derive an anonymized user data; and transmit the anonymized user data for sharing with the facility computing entity.

3. The apparatus of claim 1, wherein determining a relevance score comprises executing a rule-based relevancy scoring module based at least in part on one or more rules generated for the facility.

4. The apparatus of claim 1, wherein determining the relevance score comprises executing a machine-learning based relevance scoring model trained based at least in part on training data generated in relation to the facility.

5. The apparatus of claim 1, wherein the proposed user dataset that satisfies the facility-specific user data parameters identifies one or more health conditions of the user comprising one or more of: allergies, vaccinations, immunizations, environmental sensitivities, disabilities, diseases, eating habits, disease susceptibility, stress response, skin disorders, injuries, heart rate, or medications taken by the user.

6. The apparatus of claim 1, wherein generating the proposed user dataset in response to the request further causes the apparatus to:

generate queries to a data monitoring database to locate potential user data satisfying the facility-specific user data parameters;

identify user data satisfying one or more of the facility-specific user data parameters; and populate the proposed user dataset based at least in part on the user data identified as satisfying the one or more of the facility-specific user data parameters.

7. The apparatus of claim 1, wherein determining the sharing eligibility of the proposed user dataset further causes the apparatus to perform at least the following:

transmit for presentation the proposed user dataset to a display of the computing entity which is associated with the user; and enable the user to approve or deny the sharing eligibility of the proposed user dataset.

8. A method for selectively and securely share user data to enable accommodation of specific needs of a user, the method comprising:

receiving, by one or more processors, location information corresponding to the location of a user computing entity associated with a user;

responsive to determining that the location information indicates the location of the user computing entity as being within a proximity distance of a facility, generating, by the one or more processors, in association with a facility computing entity associated with the facility, a request for user data associated with the user of the user computing entity that is applicable to the facility, wherein the request comprises facility-specific user data parameters corresponding to characteristics of the user as indicated by at least a portion of the user data;

in response to receiving a response to the request that satisfies the facility-specific user data parameters, generating, by the one or more processors, a proposed user dataset;

determining, by the one or more processors and based at least in part on the proposed user dataset that satisfies the facility-specific user data parameters and additional user data indicative of a current context of the user, a relevance score of the proposed user dataset that satisfies the facility-specific user data parameters;

determining, by the one or more processors and based at least in part on user-specified eligibility criteria, sharing eligibility of the proposed user dataset that meets the facility-specific user data parameters based; and determining, by the one or more processors and based at least in part on the proposed user dataset that satisfies the facility-specific user data parameters for sharing with the facility, a facility adjustment plan to accommodate specific needs of the user; and responsive to determining that the relevance score satisfies applicable relevance criteria and the user specified eligibility criteria, transmitting, by the one or more processors, the proposed user dataset and the facility adjustment plan.

9. The method of claim 8, further comprising:

prior to transmitting the proposed user dataset that meets the facility-specific user data parameters for sharing with the facility, anonymizing the proposed user dataset that satisfies the facility-specific user data parameters to derive an anonymized user data; and transmitting the anonymized user data for sharing with the facility computing entity.

10. The method of claim 8, wherein determining a relevance score comprises executing a rule-based relevancy scoring module based at least in part on one or more rules generated for the facility.

11. The method of claim 8, wherein determining the relevance score comprises executing a machine-learning based relevance scoring model trained based at least in part on training data generated in relation to the facility.

12. The method of claim 8, wherein the proposed user dataset that satisfies the facility-specific user data parameters identifies one or more health conditions of the user comprising one or more of: allergies, vaccinations, immunizations, environmental sensitivities, disabilities, diseases, eating habits, disease susceptibility, stress response, skin disorders, injuries, heart rate, or medications taken by the user.

13. A computer program product comprising a non-transitory computer readable medium having computer program instructions stored therein, the computer program instructions when executed by a processor, cause the processor to:
  receive location information corresponding to the location of a user computing entity associated with a user;
  responsive to determining that upon detecting the location information indicates the location of the user computing entity as being within a proximity distance of a facility, generate, in association with a facility computing entity associated with the facility, a request for user data associated with the user of the user computing entity that is applicable to the facility, wherein the request comprises facility-specific user data parameters corresponding to characteristics of the user as reflected by at least a portion of the user data;
  in response to receiving a response to the request that satisfies the facility-specific user data parameters, generate a proposed user dataset;
  determine, based at least in part on the proposed user dataset that satisfies the facility-specific user data parameters and additional user data indicative of a current context of the user, a relevance score of the proposed user dataset that satisfies the facility-specific user data parameters;
  determine, based at least in part on user-specified eligibility criteria, sharing eligibility of the proposed user dataset that meets the facility-specific user data parameters based; and
  determine, based at least in part on the proposed user dataset that satisfies the facility-specific user data parameters for sharing with the facility, a facility adjustment plan to accommodate specific needs of the user; and
  responsive to determining that the relevance score satisfies applicable relevance criteria and the user specified eligibility criteria, transmit the proposed user dataset and the facility adjustment plan.

14. The computer program product of claim 13, wherein the computer program instructions further cause the processor to:
  prior to transmitting the proposed user dataset that meets the facility-specific user data parameters for sharing with the facility, anonymize the proposed user dataset that satisfies the facility-specific user data parameters to derive an anonymized user data; and
  transmit the anonymized user data for sharing with the facility computing entity.

15. The computer program product of claim 13, wherein determining a relevance score comprises executing a rule-based relevancy scoring module based at least in part on one or more rules generated for the facility.

16. The computer program product of claim 13, wherein determining the relevance score comprises executing a machine-learning based relevance scoring model trained based at least in part on training data generated in relation to the facility.

17. The computer program product of claim 13, wherein the proposed user dataset that satisfies the facility-specific user data parameters identifies one or more health conditions of the user comprising one or more of: allergies, vaccinations, immunizations, environmental sensitivities, disabilities, diseases, eating habits, disease susceptibility, stress response, skin disorders, injuries, heart rate, or medications taken by the user.

* * * * *

UNITED STATES PATENT AND TRADEMARK OFFICE
CERTIFICATE OF CORRECTION

PATENT NO. : 11,354,319 B2  
APPLICATION NO. : 16/777784  
DATED : June 7, 2022  
INVENTOR(S) : Muse et al.

Page 1 of 1

It is certified that error appears in the above-identified patent and that said Letters Patent is hereby corrected as shown below:

In the Claims

<u>Column 43</u>  
Line 8, "responsive to determining that upon detecting the location" should read --responsive to determining that the location--  
Lines 29-30, "dataset that meets the facility-specific user data parameters based; and" should read --dataset that meets the facility-specific user data parameters; and--

Signed and Sealed this  
Fifth Day of July, 2022

Katherine Kelly Vidal  
*Director of the United States Patent and Trademark Office*